(12) United States Patent
Parolaro et al.

(10) Patent No.: US 9,675,654 B2
(45) Date of Patent: Jun. 13, 2017

(54) PHYTOCANNABINOIDS IN THE TREATMENT OF CANCER

(71) Applicants: GW Pharma Limited, Salisbury (GB); Otsuka Pharmaceutical Co., Limited, Tokyo (JP)

(72) Inventors: Daniela Parolaro, Varese (IT); Paola Massi, Milan (IT); Angelo Antonio Izzo, Naples (IT); Francesca Borrelli, Naples (IT); Gabriella Aviello, Naples (IT); Vincenzo Di Marzo, Pozzuoli (IT); Luciano De Petrocellis, Pozzuoli (IT); Aniello Schiano Moriello, Pozzuoli (IT); Alessia Ligresti, Pozzuoli (IT); Ruth Alexandra Ross, Aberdeen (GB); Lesley Ann Ford, Aberdeen (GB); Sharon Anavi-Goffer, Aberdeen (GB); Manuel Guzman, Madrid (ES); Guillermo Velasco, Madrid (ES); Mar Lorente, Madrid (ES); Sofia Torres, Madrid (ES); Tetsuro Kikuchi, Osaka (JP); Geoffrey Guy, Salisbury (GB); Colin Stott, Salisbury (GB); Stephen Wright, Salisbury (GB); Alan Sutton, Salisbury (GB); David Potter, Salisbury (GB); Etienne De Meijer, Salisbury (GB)

(73) Assignees: GW Pharma Limited, Salisbury (GB); Otsuka Pharmaceutical Co., Limited, Tokyo (JP)

( * ) Notice: Subject to any disclaimer, the term of this patent is extended or adjusted under 35 U.S.C. 154(b) by 13 days.

(21) Appl. No.: 14/260,876

(22) Filed: Apr. 24, 2014

(65) Prior Publication Data

US 2015/0086653 A1 Mar. 26, 2015

Related U.S. Application Data

(63) Continuation of application No. 13/634,343, filed as application No. PCT/GB2011/050487 on Mar. 11, 2011, now Pat. No. 8,790,719.

(30) Foreign Application Priority Data

Mar. 12, 2010 (GB) .................................. 1004137.4

(51) Int. Cl.
| | | |
|---|---|---|
| *A01N 65/00* | (2009.01) | |
| *A61K 36/185* | (2006.01) | |
| *A61K 31/05* | (2006.01) | |
| *A61K 31/192* | (2006.01) | |
| *A61K 31/337* | (2006.01) | |
| *A61K 31/352* | (2006.01) | |
| *A61K 45/06* | (2006.01) | |
| *A61K 31/01* | (2006.01) | |
| *A61K 31/015* | (2006.01) | |
| *A61K 31/495* | (2006.01) | |

(52) U.S. Cl.
CPC ............ *A61K 36/185* (2013.01); *A61K 31/01* (2013.01); *A61K 31/015* (2013.01); *A61K 31/05* (2013.01); *A61K 31/192* (2013.01); *A61K 31/337* (2013.01); *A61K 31/352* (2013.01); *A61K 31/495* (2013.01); *A61K 45/06* (2013.01)

(58) Field of Classification Search
CPC ...................................................... A61K 36/00
USPC ............................................................ 424/725
See application file for complete search history.

(56) References Cited

U.S. PATENT DOCUMENTS

| | | | |
|---|---|---|---|
| 6,946,150 | B2 | 9/2005 | Whittle |
| 7,968,594 | B2 | 6/2011 | Guy et al. |
| 8,632,825 | B2 | 1/2014 | Velasco Diez et al. |
| 8,790,719 | B2 | 7/2014 | Parolaro et al. |
| 2002/0137064 | A1 | 9/2002 | Desprez et al. |
| 2003/0021752 | A1 | 1/2003 | Whittle et al. |
| 2003/0158191 | A1 | 8/2003 | Travis |
| 2004/0039048 | A1 | 2/2004 | Guzman et al. |
| 2004/0049059 | A1 | 3/2004 | Mueller |
| 2004/0138293 | A1 | 7/2004 | Werner et al. |
| 2005/0165259 | A1 | 7/2005 | Martin |
| 2006/0234273 | A1 | 10/2006 | Desprez et al. |
| 2006/0247304 | A1 | 11/2006 | Guy et al. |
| 2007/0072938 | A1 | 3/2007 | Rose |
| 2008/0057117 | A1 | 3/2008 | Werner et al. |
| 2008/0262099 | A1 | 10/2008 | Whittle et al. |
| 2010/0204312 | A1 | 8/2010 | Mcallister et al. |
| 2011/0086113 | A1 | 4/2011 | Velasco Diez et al. |
| 2011/0117216 | A1 | 5/2011 | Velasco Diez et al. |
| 2012/0225136 | A1 | 9/2012 | Whittle et al. |

(Continued)

FOREIGN PATENT DOCUMENTS

| | | |
|---|---|---|
| CN | 1976690 A | 6/2007 |
| EP | 1 177 790 A1 | 2/2002 |
| EP | 1 802 274 B1 | 9/2008 |

(Continued)

OTHER PUBLICATIONS

International Search Report for PCT/GB2005/003793 mailed Jan. 16, 2006.

(Continued)

*Primary Examiner* — Michael Meller
(74) *Attorney, Agent, or Firm* — Wolf, Greenfield & Sacks, P.C.

(57) ABSTRACT

This invention relates to the use of phytocannabinoids, either in an isolated form or in the form of a botanical drug substance (BDS) in the treatment of cancer. Preferably the cancer to be treated is cancer of the prostate, cancer of the breast or cancer of the colon.

1 Claim, 12 Drawing Sheets

(56) References Cited

U.S. PATENT DOCUMENTS

| | | |
|---|---|---|
| 2013/0059018 A1 | 3/2013 | Parolaro et al. |
| 2014/0287067 A1 | 9/2014 | Velasco Diez et al. |

FOREIGN PATENT DOCUMENTS

| | | |
|---|---|---|
| GB | 2 380 129 A | 4/2003 |
| GB | 2 238 707 A | 8/2003 |
| GB | 2 386 322 A | 9/2003 |
| GB | 2 391 865 A | 2/2004 |
| GB | 2 418 612 A | 4/2006 |
| GB | 2 438 682 A | 12/2007 |
| GB | 2 439 393 A | 12/2007 |
| GB | 2 448 535 A | 10/2008 |
| GB | 2 460 672 A | 12/2009 |
| GB | 2 471 987 A | 1/2011 |
| WO | WO 01/58445 A1 | 8/2001 |
| WO | WO 01/87295 A | 11/2001 |
| WO | WO 02/069993 A1 | 9/2002 |
| WO | WO 03/063847 A1 | 8/2003 |
| WO | WO 2004/041269 A2 | 5/2004 |
| WO | WO 2005/120478 A1 | 12/2005 |
| WO | WO 2006/037981 A1 | 4/2006 |
| WO | WO 2006/107903 A2 | 10/2006 |
| WO | WO 2008/129258 A1 | 10/2008 |
| WO | WO 2008/144475 A1 | 11/2008 |
| WO | WO 2008/146006 A1 | 12/2008 |
| WO | WO 2009/147438 A1 | 12/2009 |
| WO | WO 2009/147439 A1 | 12/2009 |

OTHER PUBLICATIONS

International Search Report and Written Opinion for PCT/GB2005/003793 mailed Apr. 4, 2006.
International Preliminary Examination Report and Written Opinion for PCT/GB2005/003793 mailed Oct. 4, 2006.
International Search Report and Written Opinion for PCT/GB2009/050620 mailed Sep. 23, 2009.
International Search Report on Patentability for PCT/GB2009/050620 mailed Sep. 9, 2010.
International Search Report and Written Opinion for PCT/GB2009/050621 mailed Aug. 27, 2009.
International Preliminary Report on Patentability for PCT/GB2009/050621 mailed Oct. 15, 2010.
Examination Report for GB1105991.2 mailed Jun. 17, 2011.
Examination Report for GB1107850.8 mailed Jun. 17, 2011.
Declaration of Sean D. McAllister and Pierre-Yves Desprez dated Nov. 26, 2012, filed in U.S. Appl. No. 12/600,553.
Exhibit A to McAllister and Desprez Declaration. Molecular Mechanisms of Cannabinoid Antitumor Activity, Grant Proposal, Forbes Norris/MDA ALS Research Center. Award notice date Apr. 5, 2005, 15 pages.
Exhibit B to McAllister and Desprez Declaration. Excel data reporting results of experiments. Nov. 26, 2012.
Exhibit C to McAllister and Desprez Declaration. Soroceanu et al., The role of ID-1 in modulating brain tumor invasion and dispersal. Neuro-Oncology, 2009;11:564. Abstract #3.
The United Kingdom Parliament, Select Committee on Science and Technology Ninth Report (1998) at http://www.parliament.the-stationary-office.co.uk/pa/Id199798/Idselect/Idsctech/151/15101.htm.
The United Kingdom Parliament, Select Committee on Science and Technology Second Report (Mar. 14, 2001) at http://www.publications.parliament.uk/pa/Id200001/Idselect/Idsetech/50/5001.htm.
Adalpe et al., Models of malignant glioma. Drug Discovery Today: Disease Models. 2006;3(2):191-6.
Ben-Shabat et al., New cannabidiol derivatives: synthesis, binding to cannabinoid receptor, and evaluation of their antiinflammatory activity. J Med Chem. Feb. 9, 2006;49(3):1113-7.
Blazquez, C. et al., "Inhibition of tumor angiogenesis by cannabinoids," FASEB J. 2003; 17:529-531.
Blow, Cell migration: our protruding knowledge. Nat Meth. 2007;4:589-94.
Boyden. The chemotactic effect of mixtures of antibody and antigen on polymorphonuclear leucocytes. J Exp Med. Mar. 1, 1962;11:453-66.
Casanova, M.L. et al., "Inhibition of skin tumor growth and angiogensis in vivo by activation of cannabinoid receptors," J. Clinical Investigation Jan. 1, 2003; 111(1): 43-50.
Chang et al., Signal transduction mediated by the Ras/Raf/MEK/ERK pathway from cytokine receptors to transcription factors: potential targeting for therapuetic intervention. Leukemia. Jul. 2003;17(7):1263-93.
De Meijer at al., The inheritance of chemical phenotype in *Cannabis sativa* L. (II): Cannabigerol predominant plants. Euphytica. 2005;145:189.
De Petrocellis et al., Regulation of transient receptor potential channels of melastatin type 8 (TRPM8): effect of cAMP, cannabinoid CB(1) receptors and endovanilloids. Exp Cell Res. May 15, 2007;313(9):1911-20. Epub Jan. 18, 2007.
Galve-Roperh I. et al., "Anti-tumoral action of cannabinoids: involvement of sustained ceramide accumulation and extracellular signal-regulated kinase activation," Nature Medicine Mar. 2000; 6(3): 313-319.
Gilbert et al., A phase II study of temozolomide in patients with newly diagnosed supratentorial malignant glioma before radiation therapy. Neuro Oncol. Oct. 2002;4(4):261-7.
Grotenhermen F., "Pharmacokinetics and Pharmacodynamics of Cannabinoids,"Clin Pharmacokinet. 2003;42(4):327-60.
Guzman et al., Control of the cell survival/death decision by cannabinoids. J Mol Med (Berl). 2001;78(11):613-25.
Guzmán, Cannabinoids: potential anticancer agents. Nat Rev Center. Oct. 2003;3(10):745-55.
Huang et al., ECRG2 inhibits cancer cell migration, invasion and metastasis through the down-regulation of uPA/plasmin activity. Carcinogenesis. Nov. 2007;28(11):2274-81. Epub Jun. 29, 2007.
Hulkower et al., Cell migration and invasion assays as tools for discovery. Pharmaceutics. 2011;3:107-24.
Izzo et al., Increased endocannabinoid levels reduce the development of precancerous lesions in the mouse colon. J Mol Med (Berl). Jan. 2008;86(1):89-98.
Jacobsson et al., Serum-dependent effects of tamoxifen and cannabinoids upon C6 glioma cell viability. Biochem Pharmacol. Dec. 15, 2000;60(12):1807-13.
Jacobsson, S.O.P. et al., "Inhibition of rat C6 glioma cell proliferation by endogenous and synthetic cannabinoids. Relative involvement of cannabinoid and vanilloid receptors" J. Pharmacology and Expt. Therapeutics 2001; 299(3):951-959.
Jones et al., Cannabinoid receptor systems: therapeutic targets for tumour intervention. Expert Opin Ther Targets. Dec. 2003;7(6):749-58.
Kelly et al., Tumor growth need not be driven by rare cancer stem cells. Science. Jul. 20, 2007;317(5836):337.
Killestein et al., Safety, tolerability, and efficacy of orally adminstered cannabinoids in MS. Neurology. May 14, 2002;58(9):1404-7.
Levy et al., Modulation of the metastatic frequency of a marine mammary adenocarcinoma by a synthetic cannabinoid drug. Proc Amer Assoc Canc Res. 1979;20:624.
Ligresti et al., Antitumor activity of plant cannabinoids with emphasis on the effect of cannabidiol on human breast carcinoma. J Pharmacol Exp Ther. Sep. 2006;318(3):1375-87.
Massi et al., Antitumor activity of plant cannabidiol, a nonpyschoactive cannabinoid, on human glioma cell lines. J Pharmacol Exp Ther. Mar. 2004; 308(3):838-45. Epub Nov. 14, 2003.
McAllister et al., Cannabidiol as a novel inhibitor of Id-1 gene expression in aggressive breast cancer cells. Mol Cancer Ther. Nov. 2007;6(11):2921-7.
Mechoulam et al., Cannabidiol: an overview of some pharmacological aspects. J Clin Pharmacol. Nov. 2002;42(11 Suppl):11S-19S.
Nurmikko et al., Sativex successfully treats neuropathic pain characterised by allodynia: a randomised, double-blinf, placebo-controlled clinical trial. Pain. Dec. 15, 2007;133(1-3):210-20. Epub Nov. 7, 2007.

(56) References Cited

OTHER PUBLICATIONS

Portella, Giuseppe et al., "Inhibitory effects of cannabinoid CB1 receptor stimulation on tumor growth and metastatic spreading: actions on signals invloved in angiogensis and metastasis," The FASEB Journal: Official Publications of the Federation of American Societies of Experimental Biology; Sep. 2003; 17(12):1771-1773.
Robins et al., Phase 2 trial of radiation plus high-dose tamoxifen for glioblastoma multiforme: RTOG protocol BR-0021. Neuro Oncol. Jan. 2006;8(1):47-52.
Russo et al., A tale of two cannabinoids: the therapeutic rationale for combining tetrahydrocannabinol and cannabidiol. Med Hyotheses. 2006;66(2):234-46. Epub Oct. 5, 2005.
Sarfaraz et al., Cannabinoid receptor as a novel target for the treatment of prostate cancer. Cancer Res. Mar. 1, 2005;65(5):1635-41.
Strasser et al., Comparison of orally administered cannabis extract and delta-9-tetrahydrocannabinol in treating patients with cancer-related anorexia-cachexia syndrome: a multicenter, phase III, randomized, double-blind, placebo-controlled clinical trial from the Cannabis-In-Cachexia-Study-Group. J Clin Oncol. Jul. 20, 2006;24(21):3394-400.
Torres et al., A combined preclinical therapyof cannabinoids and temozolomide against glinoma. Mol Cancer Ther. Jan. 2011;10(1):90-103.
Tucker et al., Effects of cannabinoids pn L1210 murine leukemia. 1.Inhibition of DNA synthesis. Res Commun Chem Pathol Pharmacol. Aug. 1977;17(4):703-14.
Vaccani et al., Cannabidiol inhibits human glioma cell migration through a cannabinoid receptor-independent mechanism. Br J Pharmacol. Apr. 2005;144(8):1032-6.
Velasco et al., Cannabinoids and gliomas. Mol Neurobiol. Aug. 2007;36(1):60-7. Epub Jun. 28, 2007.
Velasco, G. et al.,"Hypothesis: cannabinoid therapy for the treatment of gliomas?" Neuropharmacology Sep. 2004; 47: 315-323.
Zhongshi et al., The New Development of Anti-tumor Drug. Evaluation and Analysis of Drug-Use in Hospitals of China. 2004;4(1): 8 pages.

Reconstituted BDS

Real BDS

CBD BDS alone or in combination with Taxotere in the LNCaP xenograft model

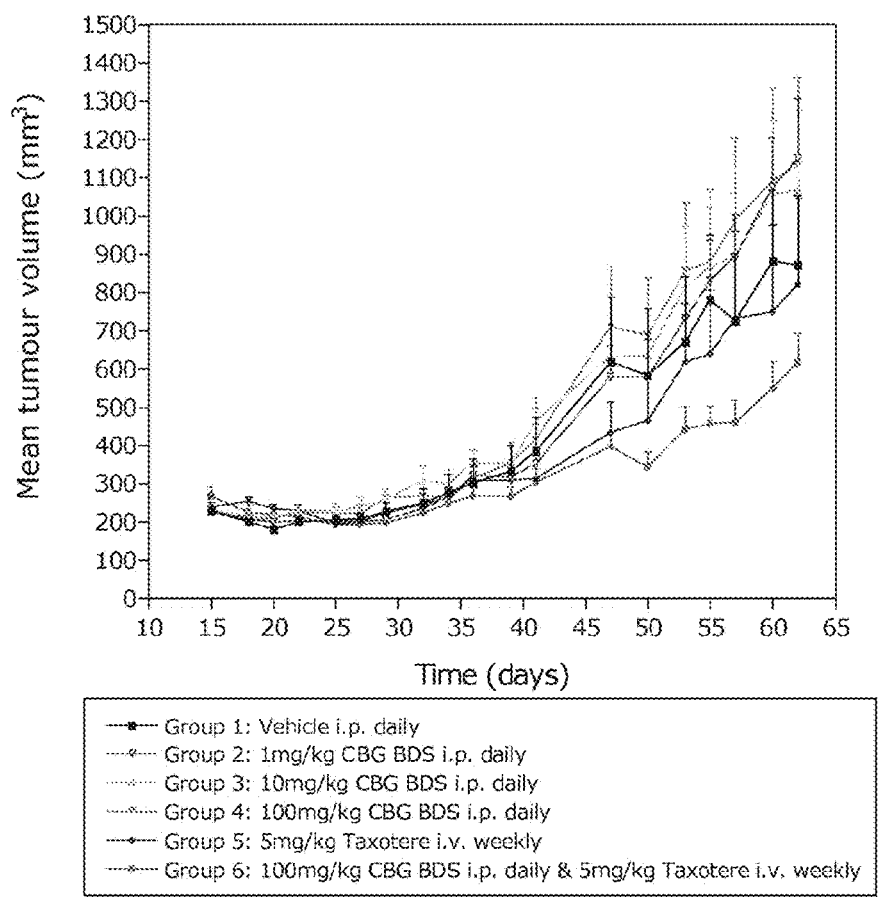

CBD BDS alone or in combination with Taxotere in the DU-145 xenograft model

Number of aberrant crypt focus (ACF) per mouse

Number of aberrant crypt focus (ACF) with 4 or more crypts per mouse

PHYTOCANNABINOIDS IN THE TREATMENT OF CANCER

RELATED APPLICATIONS

This application is a continuation of U.S. application Ser. No. 13/634,343, filed Nov. 19, 2012, which is a national stage filing under 35 U.S.C. §371 of international application PCT/GB2011/050487, filed Mar. 11, 2011, which was published under PCT Article 21(2) in English, the entire disclosures of which are incorporated herein by reference.

This invention relates to the use of phytocannabinoids, either in an isolated form or in the form of a botanical drug substance (BDS), as a prophylactic or in the treatment of cancer. Typically the cancer to be treated is a cancer of the: prostate, breast, skin, glioma, colon, lung or a bone or lymph metastasis. The phytocannabinoids may be used in combination with other cancer treatments.

BACKGROUND

Cancer is a class of diseases which occurs because cells become immortalised; they fail to heed customary signals to turn off growth which is a normal function of remodelling in the body that requires cells to die on cue. Apoptosis, or programmed cell death, can become defective and when this happens malignant transformation can take place. The immortalised cells grow beyond their normal limits and invade adjacent tissues. The malignant cells may also metastasise and spread to other locations in the body via the bloodstream or lymphatic system. Cancer cells often form a mass known as a tumour.

There are about 200 different types of cancer; the cancers can start in any type of body tissue although many cancers will metastasise into other body tissues. There are many different causes of cancer and these include; carcinogens, age, genetic mutations, immune system problems, diet, weight, lifestyle, environmental factors such as pollutants, some viruses for example the human papilloma virus (HPV) is implicated in cervical cancer and some bacterial infections are also known to cause cancers.

There are many different treatment options for cancer and the treatment sought is often determined by the type and stage of the cancer. Treatment options include; chemotherapeutic drug treatment, hormonal drug treatment, radiotherapy, surgery, complementary therapies and combinations thereof.

Prostate cancer is the most common type of cancer in men and accounts for 24% of all UK male cancers. In 2006 there were over 35,000 new cases of prostate cancer diagnosed in the UK alone.

The prostate is a gland in the male reproductive system and symptoms of cancer in the prostate can include pain, difficulty urinating, problems with sexual intercourse and erectile dysfunction. Prostate cancer may metastasise to the bones and or lymph nodes. Treatment options for prostate cancer include surgery, radiation therapy, chemotherapy and hormone treatment.

Hormone treatment usually involves treatment with an anti-androgen such as cyproterone acetate, flutamide or bicalutamide, either alone or in combination with a chemotherapeutic agent. These treatments work to stop the production of testosterone (androgen) which can slow down tumour growth or even shrink the tumour. While the prostate cancer cells are responding to anti-androgens, they are referred to as 'hormone-sensitive' prostate cancer. Unfortunately, after a few years of treatment with anti-androgens the prostate cancer stops responding to hormone treatment and is termed 'hormone-insensitive' prostate cancer. At this stage the cancer growth cannot be controlled by the hormone treatment.

In order to test the effectiveness of different compounds in the treatment of either hormone-sensitive or hormone-insensitive prostate cancer two different cell lines can be used. The cell line LNCaP are hormone-sensitive prostate cancer cells which were derived from a supraclavicular lymph node metastasis in a 50 year old male in 1977. The cell line DU-145 are hormone-insensitive prostate cancer cells which were derived from a brain metastasis.

It is known that expression levels of both cannabinoid receptors, CB1 and CB2, were significantly higher in CA-human papillomavirus-10 (virally transformed cells derived from adenocarcinoma of human prostate tissue), and other human prostate cells LNCaP, DU-145, PC3, and CWR22RN1 than in human prostate epithelial and PZ-HPV-7 (virally transformed cells derived from normal human prostate tissue) cells (Sarfaraz, 2005).

Additionally it is known that WIN-55,212-2 (mixed CB1/CB2 agonist) treatment with hormone sensitive LNCaP cells resulted in a dose- (1-10 Mmol/L) and time-dependent (24-48 hours) inhibition of cell growth. Blocking of CB1 and CB2 receptors by their antagonists SR141716 (CB1) and SR144528 (CB2) significantly prevented this effect.

These results suggested that WIN-55,212-2 or other cannabinoid receptor agonists could be developed as novel therapeutic agents for the treatment of prostate cancer.

*Cannabis* has been ascribed to be both a carcinogen and anti-cancer agent. In particular smoking *cannabis* is known to be carcinogenic as the *cannabis* smoke contains at least 50 different known carcinogenic compounds, many of which are the same substances found in smoked tobacco. One of these carcinogens, benzopyrene is known to cause cancer as it alters a gene called p53, which is a tumour suppressor gene. *Cannabis* contains the substance tetrahydrocannabinol (THC) which has been shown to cause benzopyrene to promote the p53 gene to change.

Researchers however have discovered that some cannabinoids, including THC and cannabidiol (CBD) are able to promote the re-emergence of apoptosis so that some tumours will heed the signals, stop dividing, and die. The process of apoptosis is judged by observation of several phenomena including: reduced cellular volume, condensation of nuclear chromatin, changes in distribution of phospholipids in plasma membrane phospholipids, and cleavage of chromatin into DNA fragments called DNA ladders.

Another method by which tumours grow is by ensuring that they are nourished: they send out signals to promote angiogenesis, the growth of new blood vessels. Cannabinoids may turn off these signals as well.

Cannabinoids have been shown to have an anti-proliferative effect on different cancer cell lines. The cannabinoids THC, THCA, CBD, CBDA, CBG and CBC and the cannabinoid BDS THC and CBD were tested on eight different cell lines including DU-145 (hormone-sensitive prostate cancer), MDA-MB-231 (breast cancer), CaCo-2 (colorectal cancer) and C6 (glioma cells). The data for each cannabinoid in each different type of cancer varied but generally the best data were observed with CBD or CBD BDS. The IC50 values for all the cannabinoids on the DU-145 were quite high inferring that none of the cannabinoids tested were particularly effective in the inhibition of hormone-insensitive prostate cancer (Ligresti, 2006).

Several transient receptor potential (TRP) channels have been implicated in the survival, growth and spread of prostate and other cancers. TRPM8 is expressed in sensory neurons, where it responds to cold and to cooling agents, notably menthol, but it is also abundantly expressed in the prostate. In particular TRPM8 is over-expressed in hormone-sensitive prostate cancer cells, but expression of TRPM8 is almost completely ablated once the cancer becomes hormone-insensitive and in patients receiving anti-androgen therapy. Expression of TRPM8 is stimulated by androgens in hormone-sensitive prostate cancer cell lines (LNCaP). There is evidence that expression of TRPM8 is required for survival of prostate cancer cells.

The mechanism of such an action of TRPM8 is likely to relate to its ability to modulate intracellular calcium, and possibly even the distribution of calcium within the cell. The latter point may be important because of the localisation of TRPM8 in the prostate cancer cell. While found on the cell membrane, it is also found on the endoplasmic reticulum; thus any potential therapeutic agent which targets the TRPM8 receptor must be able to gain good access to the intracellular space.

The endogenous cannabinoid anandamide has been shown to antagonise TRPM8 (De Petrocellis, 2007). The authors also showed that stimulation of CB1 receptors transiently antagonised TRPM8 receptors expressed on the same cells.

The application WO 2008/129258 describes the use of cannabinoid-containing plant extracts in the prevention or treatment of diseases or conditions that are alleviated by blockade of one or more types of TRP channel. Different binding potentials of the cannabinoid-containing plant extracts at the TRPA1 and TRPM8 channels are described. The diseases and conditions to be prevented or treated include: neuropathic pain, inflammation, vasoconstriction or cancer.

The TRPM8 receptor has also been found in breast, colon and skin cancers.

It has been shown that CBD is able to able to down-regulate the expression of the DNA binding protein inhibitor, Id-1 in human breast cancer cells (McAllister, 2007). The CBD concentrations effective at inhibiting Id-1 expression correlated with those used to inhibit the proliferative and invasive phenotype of breast cancer cells. CBD was able to inhibit Id-1 expression at the mRNA and protein level in a concentration-dependent fashion.

CBD has also been shown to inhibit human cancer cell proliferation and invasion through differential modulation of the ERK and ROS pathways, and that sustained activation of the ERK pathway leads to down-regulation of Id-1 expression. It was also demonstrated that CBD up-regulates the pro-differentiation agent, Id-2. Using a mouse 4T1 cell line and a model of metastatic breast cancer, CBD significantly reduced metastatic spread. As such CBD may represent a promising treatment of breast cancer in patients with secondary tumours (McAllister, 2009).

Recent evidence indicates that CBD is a GPR55 antagonist; this raises the possibility that this receptor may underlie the effects of CBD on breast and other tumour cells. GPR55 couples to G12/13 and the downstream activation of the RhoA, rac1 and cdc42 small GTPases; this pathway is crucial in cytoskeletal reorganisation and cell migration. Increased G12/13 expression has been found in early stage human breast cancer cells taken by biopsy and inhibition of G13 decreases the level of breast cancer cell metastasis in vivo (Kelly et al, 2007).

The anti-proliferative effects of CBD have also been evaluated on U87 and U373 human glioma cell lines, (Massi, 2004). The anti-proliferative effect of CBD was correlated to induction of apoptosis, as determined by cyto-fluorimetric analysis and single-strand DNA staining, which was not reverted by cannabinoid antagonists. In addition CBD, administered s.c. to nude mice at the dose of 0.5 mg/mouse, significantly inhibited the growth of subcutaneously implanted U87 human glioma cells. It was concluded that CBD was able to produce a significant anti-tumour activity both in vitro and in vivo, thus suggesting a possible application of CBD as a chemotherapeutic agent.

The application WO/2006/037981 describes the use of the cannabinoid CBD to prevent tumour cells migrating or metastisising from an area of uncontrolled growth to an area away from the original tumour site. CBD caused a concentration-dependent inhibition of the migration of U87 glioma cells, quantified in a Boyden chamber. Since these cells express both cannabinoid CB1 and CB2 receptors in the membrane, the group also evaluated their engagement in the anti-migratory effect of CBD.

Cannabinoids have been shown to play a fundamental role in the control of cell survival/cell death. It has been reported that cannabinoids may induce proliferation, growth arrest, or apoptosis in a number of cells, including neurons, lymphocytes, and various transformed neural and non-neural cells, and that cannabinoids induce apoptosis of glioma cells in culture and regression of malignant gliomas in vivo (Guzman, 2001).

A pilot clinical study of THC in patients with recurrent glioblastoma multiforme has been conducted. This pilot phase I trial consisted of nine patients with recurrent glioblastoma multiforme who were administered THC intratumourally. The patients had previously failed standard therapy (surgery and radiotherapy) and had clear evidence of tumour progression. The primary end point of the study was to determine the safety of intracranial THC administration. They also evaluated THC action on the length of survival and various tumour-cell parameters. Median survival of the cohort from the beginning of cannabinoid administration was 24 weeks (95% confidence interval: 15-33).

The application WO 2008/144475 describes treating cell proliferation disorders including cancer with cannabidiol derivatives either alone or in combination with THC or a derivative thereof.

The application WO 03/063847 describes the use of CBDA or CBDVA as an active pharmaceutical substance. The focus of the application provides a treatment for nausea, vomiting emesis and motion sickness.

The application WO 2009/147439 describes the use of a combination of cannabinoids, particularly tetrahydrocannabinol (THC) and cannabidiol (CBD), in the manufacture of a medicament for use in the treatment of cancer. In particular the cancer to be treated is a brain tumour, more particularly a glioma; more particularly still a glioblastoma multiforme (GBM).

The application WO 2009/147438 describes the use of one or more cannabinoids, particularly THC and/or CBD in combination with a non-cannabinoid chemotherapeutic agent in the manufacture of a medicament for use in the treatment of cancer. In particular the cancer to be treated is a brain tumour, more particularly a glioma, more particularly still a glioblastoma multiforme (GBM). The non-cannabinoid chemotherapeutic agent may be a selective estrogen receptor modulator or an alkylating agent.

The literature and corresponding patent applications demonstrate the general usefulness of cannabinoids in the area of cancer research and treatment.

It is an object of the present invention to find improved and/or alternative cancer therapies. To this end a platform of data representing the use of isolated phytocannabinoids and phytocannabinoid botanical drug substances (BDS) in different aspects of the treatment of cancer is provided and the results extrapolated to identify groups of phytocannabinoids, whether isolated or in the form of a BDS, which appear more promising than others in specific treatments.

DEFINITIONS AND ABBREVIATIONS

Definitions of some of the terms used to describe the invention are detailed below:

The phytocannabinoids described in the present application are listed below along with their standard abbreviations.

| CBC | Cannabichromene |
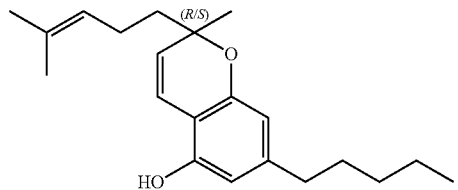 [SMILES: CCCCCc1cc(O)c2c(c1)OC(C)(CCC=C(C)C)C=C2]

| CBCV | Cannabichromenic acid |
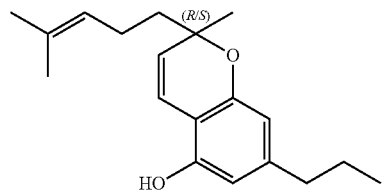 [SMILES: CCCc1cc(O)c2c(c1)OC(C)(CCC=C(C)C)C=C2]

| CBD | Cannabidiol |
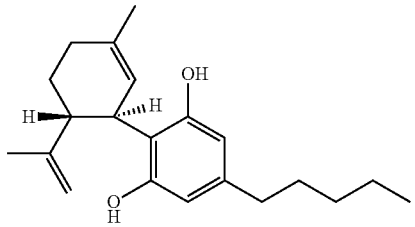 [SMILES: C=C(C)[C@@H]1CCC(C)=C[C@H]1c1c(O)cc(CCCCC)cc1O]

| CBDA | Cannabidiolic acid |
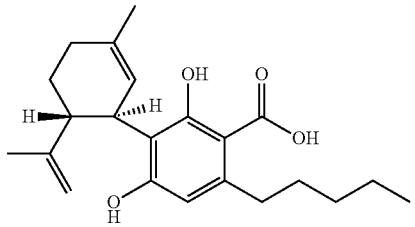 [SMILES: C=C(C)[C@@H]1CCC(C)=C[C@H]1c1c(O)cc(CCCCC)c(C(=O)O)c1O]

| CBDV | Cannabidivarin |
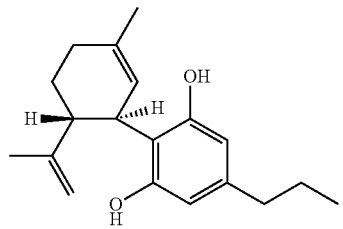 [SMILES: C=C(C)[C@@H]1CCC(C)=C[C@H]1c1c(O)cc(CCC)cc1O]

| CBG | Cannabigerol |
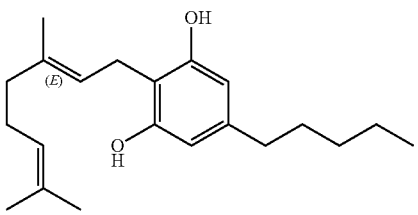 [SMILES: CCCCCc1cc(O)c(C/C=C(\C)CCC=C(C)C)c(O)c1]

-continued
| | | |
|---|---|---|
| CBGV | Cannabigerol propyl variant | 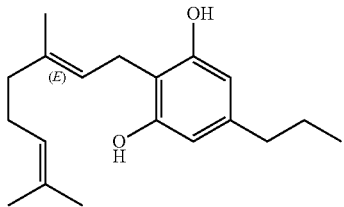 [SMILES: CCCc1cc(O)c(C/C=C(\C)CCC=C(C)C)c(O)c1] |
| CBL | Cannabicyclol | 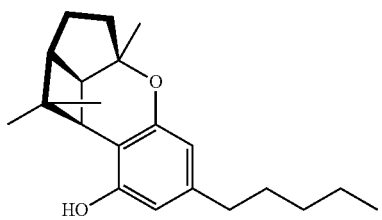 |
| CBN | Cannabinol | 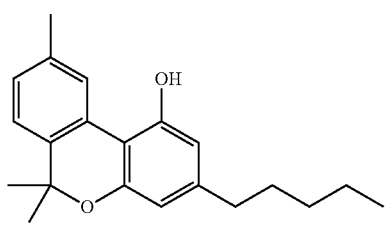 [SMILES: CCCCCc1cc(O)c2c(c1)OC(C)(C)c1ccc(C)cc1-2] |
| CBNV | Cannabinol propyl variant | 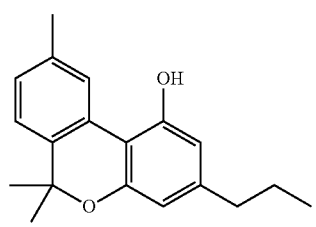 [SMILES: CCCc1cc(O)c2c(c1)OC(C)(C)c1ccc(C)cc1-2] |
| CBO | Cannabitriol | 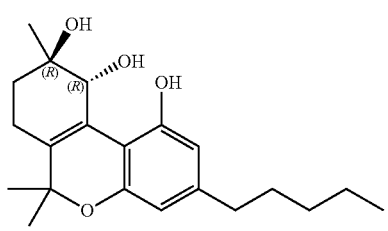 |
| THC | Tetrahydrocannabinol | 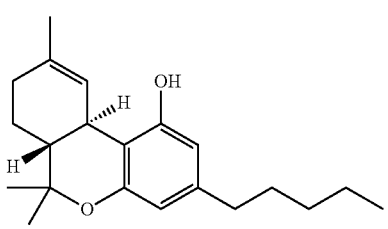 [SMILES: CCCCCc1cc(O)c2c(c1)OC(C)(C)[C@@H]1CCC(C)=C[C@@H]21] |
| THCA | Tetrahydrocannabinolic acid | 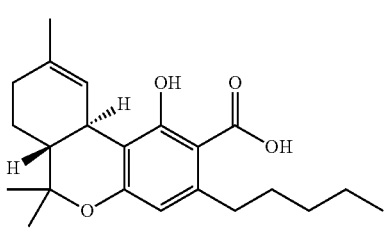 [SMILES: CCCCCc1cc2c(c(O)c1C(=O)O)[C@@H]1C=C(C)CC[C@H]1C(C)(C)O2] |

| | |
|---|---|
| THCV Tetrahydrocannabivarin | 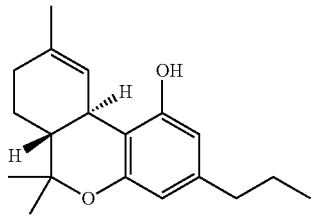 [SMILES: CCCc1cc(O)c2c(c1)OC(C)(C)[C@@H]1CCC(C)=C[C@@H]21] |
| THCVA Tetrahydrocannabivarinic acid | 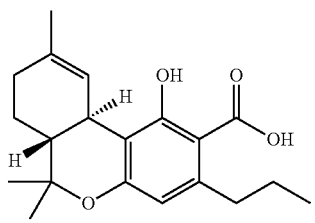 [SMILES: CCCc1cc2c(c(O)c1C(=O)O)[C@@H]1C=C(C)CC[C@H]1C(C)(C)O2] |

The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids.

"Phytocannabinoids" are cannabinoids that originate from nature and can be found in the *cannabis* plant. The phytocannabinoids can be isolated cannabinoids or present as a botanical drug substance.

An "isolated cannabinoid" is defined as a phytocannabinoid that has been extracted from the *cannabis* plant and purified to such an extent that all the additional components such as secondary and minor cannabinoids and the non-cannabinoid fraction have been removed.

A "botanical drug substance" or "BDS" is defined in the Guidance for Industry Botanical Drug Products Draft Guidance, August 2000, US Department of Health and Human Services, Food and Drug Administration Centre for Drug Evaluation and Research as: "A drug derived from one or more plants, algae, or microscopic fungi. It is prepared from botanical raw materials by one or more of the following processes: pulverisation, decoction, expression, aqueous extraction, ethanolic extraction or other similar processes." A botanical drug substance does not include a highly purified or chemically modified substance derived from natural sources. Thus, in the case of *cannabis*, BDS derived from *cannabis* plants do not include highly purified Pharmacopoeial grade cannabinoids.

"Endocannabinoids" are the cannabinoids that are produced endogenously by human or animal bodies. Up or down regulation of the endocannabinoid system may be useful in the treatment of some diseases or conditions.

"Synthetic cannabinoids" are compounds that have a cannabinoid-like structure yet are manufactured using chemical means. Depending on the method of manufacture the synthetic cannabinoid may comprise a racemic mixture of cannabinoids, in contrast to an isolated cannabinoid which will be a single enantiomer.

Phytocannabinoids can be found as either the neutral (decarboxylated form) or the carboxylic acid form depending on the method used to extract the cannabinoids. For example it is known that heating the carboxylic acid form will cause most of the carboxylic acid form to decarboxylate into the neutral form.

Phytocannabinoids can also occur as either the pentyl (5 carbon atoms) or propyl (3 carbon atoms) variant. Initially it was thought that the propyl and pentyl variants would have similar properties, however recent research has found that this may not be true. For example the phytocannabinoid THC is known to be a CB1 receptor agonist whereas the propyl variant THCV has been discovered to be a CB1 receptor antagonist meaning that it has almost opposite effects.

In the present invention a BDS is considered to have two components: the phytocannabinoid-containing component and the non-phytocannabinoid containing component. Preferably the phytocannabinoid-containing component is the larger component comprising greater than 50% (w/w) of the total BDS and the non-phytocannabinoid containing component is the smaller component comprising less than 50% (w/w) of the total BDS.

The amount of phytocannabinoid-containing component in the BDS may be greater than 55%, through 60%, 65%, 70%, 75%, 80% to 85% or more of the total extract. The actual amount is likely to depend on the starting material used and the method of extraction used.

The "principle phytocannabinoid" in a BDS is the phytocannabinoid that is present in an amount that is higher than that of the other phytocannabinoids. Preferably the principle phytocannabinoid is present in an amount greater than 40% (w/w) of the total extract. More preferably the principle phytocannabinoid is present in an amount greater than 50% (w/w) of the total extract. More preferably still the principle phytocannabinoid is present in an amount greater than 60% (w/w) of the total extract.

The amount of the principle phytocannabinoid in the BDS is preferably greater than 75% of the phytocannabinoid-containing fraction, more preferably still greater than 85% of the phytocannabinoid-containing fraction, and more preferably still greater than 95% of the phytocannabinoid-containing fraction.

In some cases, such as where the principle cannabinoid is either CBDV or THCVA the amount of the principle phytocannabinoid in the BDS is lower. Here the amount of phytocannabinoid is preferably greater than 55% of the phytocannabinoid-containing fraction.

The "secondary phytocannabinoid/s" in a BDS is the phytocannabinoid/s that is/are present in significant proportions. Preferably the secondary phytocannabinoid is present in an amount greater than 5% (w/w) of the total extract, more preferably greater than 10% (w/w) of the total extract, more preferably still greater than 15% (w/w) of the total extract. Some BDS's will have two or more secondary phytocannabinoids that are present in significant amounts. However not all BDS's will have a secondary phytocannabinoid. For example CBG BDS does not have a secondary phytocannabinoid in its extract.

The "minor phytocannabinoid/s" in a BDS can be described as the remainder of all the phytocannabinoid components once the principle and secondary phytocannabinoids are accounted for. Preferably the minor phytocannabinoids are present in total in an amount of less than 10% (w/w) of the total extract, more preferably still less than 5% (w/w) of the total extract, and most preferably the minor phytocannabinoid is present in an amount less than 2% (w/w) of the total extract.

Typically the non-phytocannabinoid containing component of the BDS comprises terpenes, sterols, triglycerides, alkanes, squalenes, tocopherols and carotenoids.

These compounds may play an important role in the pharmacology of the BDS either alone or in combination with the phytocannabinoid.

The "terpene fraction" may be of significance and can be broken down by the type of terpene: monoterpene or sesquiterpene. These terpene components can be further defined in a similar manner to the cannabinoids.

The amount of non-phytocannabinoid containing component in the BDS may be less than 45%, through 40%, 35%, 30%, 25%, 20% to 15% or less of the total extract. The actual amount is likely to depend on the starting material used and the method of extraction used.

The "principle monoterpene/s" in a BDS is the monoterpene that is present in an amount that is higher than that of the other monoterpenes. Preferably the principle monoterpene/s is present in an amount greater than 20% (w/w) of the total terpene content. More preferably the principle monoterpene is present in an amount greater than 30% (w/w) of the total terpene content, more preferably still greater than 40% (w/w) of the total terpene content, and more preferably still greater than 50% (w/w) of the total terpene content. The principle monoterpene is preferably a myrcene or pinene. In some cases there may be two principle monoterpenes. Where this is the case the principle monoterpenes are preferably a pinene and/or a myrcene.

The "principle sesquiterpene" in a BDS is the sesquiterpene that is present in an amount that is higher than all the other terpenes. Preferably the principle sesquiterpene is present in an amount greater than 20% (w/w) of the total terpene content, more preferably still t greater than 30% (w/w) of the total terpene content. The principle sesquiterpene is preferably a caryophyllene and/or a humulene.

The sesquiterpene components may have a "secondary sesquiterpene". The secondary monoterpene is preferably a pinene, which is preferably present at an amount greater than 5% (w/w) of the total terpene content, more preferably the secondary terpene is present at an amount greater than 10% (w/w) of the total terpene content.

The secondary sesquiterpene is preferably a humulene which is preferably present at an amount greater than 5% (w/w) of the total terpene content, more preferably the secondary terpene is present at an amount greater than 10% (w/w) of the total terpene content.

Alternatively botanical extracts may be prepared by introducing isolated phytocannabinoids into a non-cannabinoid plant fraction as can be obtained from a zero cannabinoid plant or a CBG-free BDS.

BRIEF SUMMARY OF THE DISCLOSURE

In accordance with a first aspect of the present invention there is provided a *cannabis* plant extract comprising a phytocannabinoid containing component and a non-phytocannabinoid containing component, for use in medicine, wherein the phytocannabinoid containing component comprises at least 50% (w/w) of the *cannabis* plant extract and the non-phytocannabinoid containing component comprises a monoterpene fraction and a sesquiterpene fraction, in which a principle monoterpene sub-fraction is selected from myrcenes or pinenes and a principle sesquiterpene sub-fraction is selected from caryophyllenes or humulenes.

In accordance with a second aspect of the present invention there is provided the use of a *cannabis* plant extract comprising a phytocannabinoid containing component and a non-phytocannabinoid containing component, for use in the manufacture of a medicament for use in medicine, wherein the phytocannabinoid containing component comprises at least 50% (w/w) of the *cannabis* plant extract and the non-phytocannabinoid containing component comprises a monoterpene fraction and a sesquiterpene fraction, in which a principle monoterpene sub-fraction is selected from myrcenes or pinenes and a principle sesquiterpene sub-fraction is selected from caryophyllenes or humulenes.

In accordance with a third aspect of the present invention there is provided a method of treating a patient comprising administering a therapeutically effective amount of a *cannabis* plant extract comprising a phytocannabinoid containing component and a non-phytocannabinoid containing component, wherein the phytocannabinoid containing component comprises at least 50% (w/w) of the *cannabis* plant extract and the non-phytocannabinoid containing component comprises a monoterpene fraction and a sesquiterpene fraction, in which a principle monoterpene sub-fraction is selected from myrcenes or pinenes and a principle sesquiterpene sub-fraction is selected from caryophyllenes or humulenes to the patient.

Preferably principle monoterpene sub-fraction comprises myrcenes and the secondary monoterpene sub-fraction comprises pinenes. In another embodiment the principle monoterpene sub-fraction are both myrcenes and pinenes.

Preferably the principle sesquiterpene sub-fraction comprises caryophyllenes and secondary sesquiterpene sub-fraction comprises humulenes.

Preferably the principle phytocannabinoid is selected from the group consisting of: THCV, CBDV, CBGV, THCVA, THCA, CBDA, CBG, THC, CBD and CBC.

Preferably the non-phytocannabinoid containing component further comprises one or more compounds from the group consisting of: diterpenes; triterpenes; sterols; triglycerides; alkanes; squalenes; tocopherols; and carotenoids.

In one embodiment the *cannabis* plant extract comprises the principle phytocannabinoid CBG and the phytocannabinoid containing component comprises 61-75% (w/w) of the *cannabis* plant extract. Preferably the extract further comprises greater than 88% (w/w) CBG of the total phytocannabinoid fraction.

In a further embodiment the *cannabis* plant extract comprises the principle phytocannabinoid THC and the phytocannabinoid containing component comprises 77-94% (w/w) of the *cannabis* plant extract. Preferably the extract further comprises 78-95% (w/w) THC of the total phytocannabinoid fraction.

In a further embodiment the *cannabis* plant extract comprises the principle phytocannabinoid CBD and the phytocannabinoid containing component comprises 76-96%

(w/w) of the *cannabis* plant extract. Preferably the extract further comprises 72-88% (w/w) CBD of the total phytocannabinoid fraction.

In a further embodiment the *cannabis* plant extract comprises the principle phytocannabinoid CBC and the phytocannabinoid containing component comprises 49-60% (w/w) of the *cannabis* plant extract. Preferably the extract further comprises 71-87% (w/w) CBC of the total phytocannabinoid fraction. More preferably the extract further comprises the secondary phytocannabinoids CBD and CBL. More preferably still the CBD comprises 6.5-8% (w/w) of the total phytocannabinoid fraction and the CBL comprises 5.8-7.1 (w/w) of the total phytocannabinoid fraction.

In a further embodiment the *cannabis* plant extract comprises the principle phytocannabinoid THCV and the phytocannabinoid containing component comprises 74-90% (w/w) of the *cannabis* plant extract. Preferably the extract further comprises 71-87% (w/w) THCV of the total phytocannabinoid fraction. More preferably the extract further comprises the secondary phytocannabinoid THC. More preferably still the THC comprises 14.8-18% (w/w) of the total phytocannabinoid fraction.

In a further embodiment the *cannabis* plant extract comprises the principle phytocannabinoid CBDV and the phytocannabinoid containing component comprises 64-78% (w/w) of the *cannabis* plant extract. Preferably the extract further comprises 52-64% (w/w) CBDV of the total phytocannabinoid fraction. More preferably the extract further comprises the secondary phytocannabinoids CBD and CBCV. More preferably still the CBD comprises 22.4-27.4% (w/w) of the total phytocannabinoid fraction and the CBCV comprises 5.5-6.7 (w/w) of the total phytocannabinoid fraction.

In a further embodiment the *cannabis* plant extract comprises the principle phytocannabinoid CBGV and the phytocannabinoid containing component comprises 54-66% (w/w) of the *cannabis* plant extract. Preferably the extract further comprises 68-84% (w/w) CBGV of the total phytocannabinoid fraction. More preferably the extract further comprises the secondary phytocannabinoid CBG. More preferably still the CBG comprises 19-23% (w/w) of the total phytocannabinoid fraction.

In a further embodiment the *cannabis* plant extract comprises the principle phytocannabinoid THCA and the phytocannabinoid containing component comprises 54-66% (w/w) of the *cannabis* plant extract. Preferably the extract further comprises 71-86% (w/w) THCA of the total phytocannabinoid fraction. More preferably the extract further comprises the secondary phytocannabinoid THC. More preferably still the THC comprises 13.4-16.4% (w/w) of the total phytocannabinoid fraction.

In a further embodiment the *cannabis* plant extract comprises the principle phytocannabinoid CBDA and the phytocannabinoid containing component comprises 71-86% (w/w) of the *cannabis* plant extract. Preferably the extract further comprises 78-86% (w/w) CBDA of the total phytocannabinoid fraction. More preferably the extract further comprises the secondary phytocannabinoid CBD. More preferably still the CBD comprises 6.1-7.5% (w/w) of the total phytocannabinoid fraction.

In a further embodiment the *cannabis* plant extract comprises the principle phytocannabinoid THCVA and the phytocannabinoid containing component comprises 62-75% (w/w) of the *cannabis* plant extract. Preferably the extract further comprises 53-65% (w/w) THCVA of the total phytocannabinoid fraction. More preferably the extract further comprises the secondary phytocannabinoid THCV. More preferably still the THCV comprises 17.3-21.2% (w/w) of the total phytocannabinoid fraction.

In a fourth aspect of the present invention there is provided one or more phytocannabinoids, either in an isolated form or in the form of a botanical drug substance (BDS), as a prophylactic or in the treatment of cancer.

In a fifth aspect of the present invention there is provided one or more phytocannabinoids taken from the group selected from: THCV, CBDV, THCVA, THCA, CBDA, CBD, CBG, and CBC, for use in the treatment of prostate cancer, wherein the THCVA is present as an isolated phytocannabinoid, the THCA, CBDA CBD, CBG or CBC are present in the form of a BDS, and the THCV or CBDV are present in either an isolated form or in the form of a BDS.

In accordance with a sixth aspect of the present invention there is provided the use of one or more phytocannabinoids taken from the group selected from: THCV, CBDV, THCVA, THCA, CBDA, CBD, CBG, and CBC, for use in the manufacture of a medicament to treat prostate cancer, wherein the THCVA is present as an isolated phytocannabinoid, the THCA, CBDA CBD, CBG or CBC are present in the form of a BDS, and the THCV or CBDV are present in either an isolated form or in the form of a BDS.

In accordance with a seventh aspect of the present invention there is provided a method of treating a patient with prostate cancer comprising administering an effective amount of one or more phytocannabinoids, selected from the group consisting of: THCV, CBDV, THCVA, THCA, CBDA, CBD, CBG, and CBC, wherein, where present, the THCVA is present as an isolated phytocannabinoid, the THCA, CBDA, CBD, CBG or CBC are present in the form of a BDS, and the THCV or CBDV are present in either an isolated form or in the form of a BDS to the patient.

In one embodiment the one or more phytocannabinoids are propyl variant phytocannabinoids.

In a second embodiment the one or more phytocannabinoids are in an acid form.

In a further embodiment the one or more phytocannabinoids are in a neutral or decarboxylated form.

In a preferred embodiment the phytocannabinoid is CBG and is in the form of a BDS.

Preferably the prostate cancer is hormone-sensitive prostate cancer.

In another embodiment the phytocannabinoid is THCVA in an isolated form.

In a further embodiment the prostate cancer is hormone-insensitive prostate cancer and the phytocannabinoid is CBD and is in the form of a BDS or the phytocannabinoid is CBDV and is in the form of a BDS.

Preferably the one or more phytocannabinoids are used in combination or as an adjunct therapy with a chemotherapeutic agent and/or an anti-androgen.

Preferably the chemotherapeutic agent is a mitotic inhibitor. The mitotic inhibitor is preferably from the taxane drug class. More preferably the mitotic inhibitor taken from the taxane drug class is taken from the group: docetaxel; larotaxel; ortataxel; paclitaxel; and tesetaxel.

When the one or more phytocannabinoids are used in combination with a chemotherapeutic agent and or anti-androgen the phytocannabinoid is preferably CBG or CBD, which may be in the form of a BDS.

In a further embodiment the one or more phytocannabinoids are used for the purpose of slowing down the growth or reducing the volume of a prostate cancer tumour.

In accordance with a eighth aspect of the present invention there is provided the use of one or more propyl phytocannabinoids or acid phytocannabinoids for use in the down regulation of ERK signalling and effect one or more of: anti-proliferation, anti-metastasis or anti-angiogenesis in a human patient.

In accordance with a ninth aspect of the present invention there is provided the use of one or more propyl phytocannabinoids or acid phytocannabinoids in the manufacture of a medicament to down regulate ERK signalling and effect one or more of: anti-proliferation, anti-metastasis or anti-angiogenesis in a human patient.

In accordance with a tenth aspect of the present invention there is provided a method of treating a patient with cancer comprising administering one or more propyl phytocannabinoids or acid phytocannabinoids to down regulate ERK signalling and effect one or more of: anti-proliferation, anti-metastasis or anti-angiogenesis to the patient.

Preferably the one or more phytocannabinoids are selected from the group consisting of: THCV, CBGV, CBDV, CBGA and CBDA.

Preferably the one or more phytocannabinoids are in an isolated form.

Preferably the one or more propyl or acid phytocannabinoids are for use in the treatment of lung cancer, prostate cancer, or breast cancer.

Preferably the one or more propyl or acid phytocannabinoids are for use in the treatment of bone or lymph metastasis.

In accordance with a eleventh aspect of the present invention there is provided the use of one or more phytocannabinoid acids, excluding CBDA or CBDVA, for use in medicine.

In accordance with an twelfth aspect of the present invention there is provided the use of the one or more phytocannabinoid acids for use in the treatment of cancer.

In accordance with a thirteenth aspect of the present invention there is provided the use of one or more phytocannabinoid acids in the manufacture of a medicament for use in the treatment of cancer.

In accordance with a fourteenth aspect of the present invention there is provided a method of treating a patient with cancer comprising administering a therapeutic amount of one or more phytocannabinoid acids to the patient.

Preferably the one or more phytocannabinoid acids are in the form of a BDS.

Preferably the cancer to be treated is a cancer of the prostate, breast, colon, lung, glioma or skin.

Preferably the phytocannabinoid acid is taken from the group consisting of: THCA, CBGA and CBDA.

More preferably there is provided a combination of the phytocannabinoid THCA with CBDA and/or CBGA.

In accordance with a fifteenth aspect of the present invention there is provided an isolated CBD, CBG, CBDV, CBD BDS, CBG BDS and/or CBDV BDS for use in the treatment of a pre-cancerous symptom of colon cancer.

In accordance with a sixteenth aspect of the present invention there is provided the use of an isolated CBD, CBG, CBDV, CBD BDS, CBG BDS and/or CBDV BDS in the manufacture of a medicament to treat a pre-cancerous symptom of colon cancer.

In accordance with a seventeenth aspect of the present invention there is provided a method of treating a patient with a pre-cancerous symptom of colon cancer, comprising administering a therapeutically effective amount of an isolated CBD, CBG, CBDV, CBD BDS, CBG BDS and/or CBDV BDS to the patient.

In one embodiment the isolated CBD, CBG, CBDV, CBD BDS, CBG BDS and/or CBDV BDS are used in the treatment of aberrant crypts in the colon.

In a further embodiment the isolated CBD, CBG, CBDV, CBD BDS, CBG BDS and/or CBDV BDS are used in the treatment of colon polyps.

In accordance with a eighteenth aspect of the present invention there is provided a combination of phytocannabinoids together with a chemotherapeutic agent which is not a cannabinoid, for use in the treatment of a glioma.

In accordance with a nineteenth aspect of the present invention there is provided the use of a combination of phytocannabinoids together with a chemotherapeutic agent which is not a cannabinoid, in the manufacture of a medicament to treat a glioma.

In accordance with a twentieth aspect of the present invention there is provided a method of treating a patient with a glioma, comprising administering a therapeutically effective amount of a combination of phytocannabinoids together with a chemotherapeutic agent which is not a cannabinoid, to the patient.

Preferably the combination of phytocannabinoids and the chemotherapeutic agent which is not a cannabinoid are packaged for administration separately, simultaneously or sequentially.

Preferably the phytocannabinoids are THC and CBD.

Preferably the dose level of the phytocannabinoids is sub-effective for the treatment of the glioma if used alone.

Preferably the chemotherapeutic agent is temazolamide.

Preferably the dose level of the temazolamide is sub-effective for the treatment of glioma if used alone.

BRIEF DESCRIPTION OF THE DRAWINGS

Embodiments of the invention are further described hereinafter with reference to the accompanying drawings, in which:

FIGS. 4A-4D show the effect of cannabinoids alone or in combination with a chemotherapeutic agent in hormone-insensitive prostate cancer cell line (DU-145) and hormone-sensitive prostate cancer cell line (LNCaP) in a subcutaneous xenograft model;

DETAILED DESCRIPTION

The use of phytocannabinoids, either isolated or with all their co-extracted components is described in the following examples.

Example 1

Botanical Production and Manufacture of Cannabinoid BDS

Botanical Raw Material (BRM) is obtained from varieties of *Cannabis sativa* L. (chemotypes) which have been developed to specifically produce high levels of a given phytocannabinoid as the principal phytocannabinoid. The cannabinoid CBG is the precursor molecule in the biosynthetic pathway to THC, CBD and CBC. Other cannabinoids are then formed from these cannabinoids. The principal cannabinoid produced in the plant will be present as the carboxylic acid form in the plant material, as are any of the other secondary or minor cannabinoids. The carboxylic acid form of the cannabinoid is usually decarboxylated to the neutral form during processing of the BRM to Botanical Drug Substance (BDS).

The plants used to prepare the cannabinoid BDS can either be wild type plants or plants specifically bred to produce one cannabinoid as a principle cannabinoid. These plants are referred to as 'chemotypes'. For example the paper by (De Meijer & Hammond, 2005) describes the selective breeding of a plant high in CBG. Wild type plants that produce a large amount of CBG have been found in European fibre hemp populations.

Figure 1:
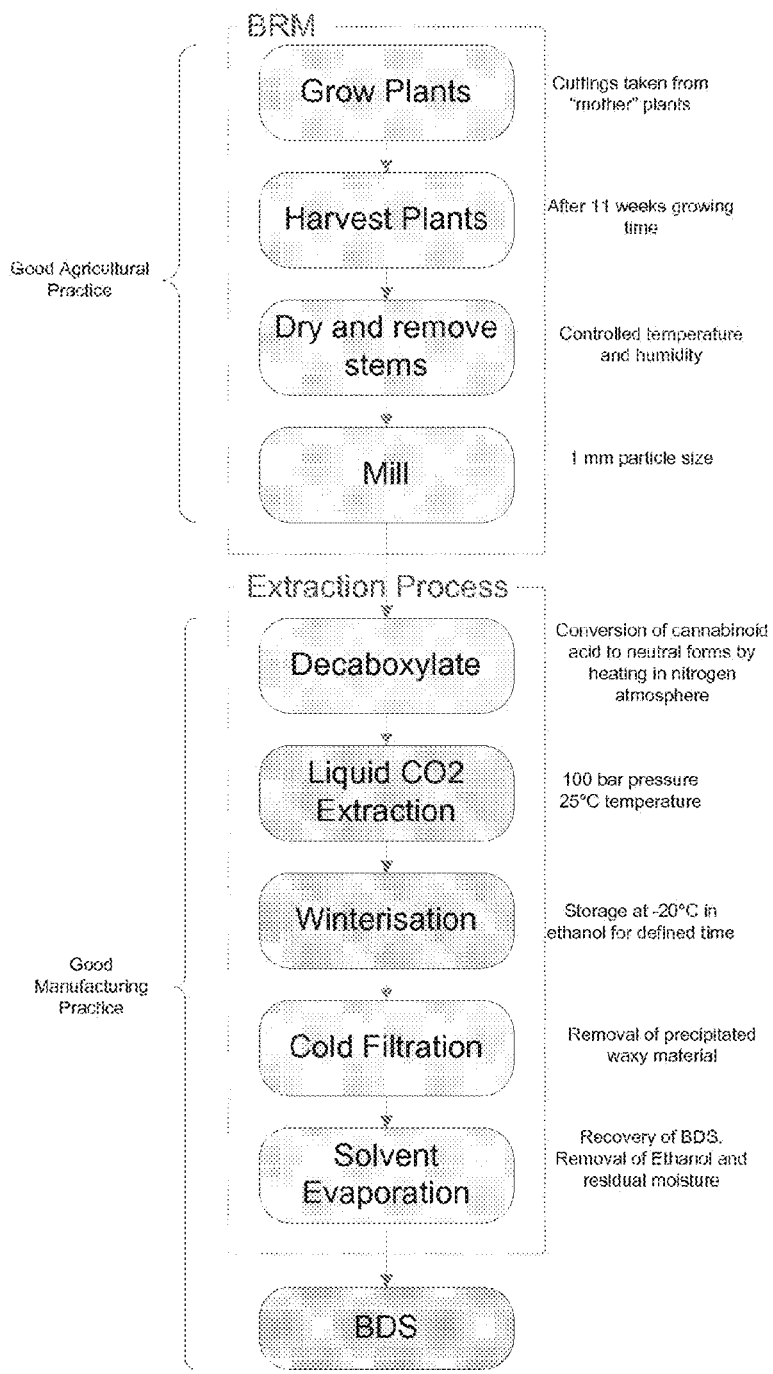
FIG. 1 shows an overview of Botanical Drug Substance (BDS) preparation.

Botanical Drug Substance (BDS) are prepared from BRM and are extracts suitable for further formulation and/or investigative purposes. These extracts are termed a Botanical Drug Substance. A brief overview of the method is provided in FIG. 1. Conditions for the extraction process are optimised to give the most favourable balance of cannabinoid content and non-cannabinoid fraction along with satisfactory yield. For example the cannabinoid content of the CBG BDS is virtually 100% CBG, with only very small quantities of other cannabinoids present.

Cannabinoid free BDS can be prepared from CBG BDS or a zero cannabinoid plant such as USO-31. Because CBG is the major cannabinoid present in CBG BDS it is possible to remove the CBG present relatively easily using standard techniques known in the art such as column chromatography. A CBG-free extract can be used to assess what pharmacology if any, there is associated with the non-cannabinoid fraction. It is possible to fractionate the BDS completely so that individual compounds can be removed for purification and the remainder recombined to produce, following solvent removal, a BDS free of the selected compound(s). The CBG free extract thus produced allows for the evaluation of any synergy between the cannabinoid and non-cannabinoid fractions.

Isolated phytocannabinoids can also be prepared. As indicated above column chromatography may be used to isolate CBG from CBG BDS to produce purity greater than 99%. The BDS and the isolated phytocannabinoid can then be used to compare the effectiveness and any synergy between the principle phytocannabinoid and the other phytocannabinoids and non-cannabinoid constituents in the BDS.

Example 2

Phytocannabinoid and Non-Cannabinoid Components in BDS

The following example illustrates the different phytocannabinoid components that make up each of the BDS's described. In each table the principle phytocannabinoid is defined in bold typeface.

The BDS's were extracted using liquid $CO_2$ and then a high performance liquid chromatography (HPLC) method was used to analyse the different cannabinoid components in each cannabinoid BDS.

The tables detailed below describe average amounts of the principle, secondary and minor phytocannabinoids in each representative BDS. The skilled person will appreciate that as the BDS's are extracted from *cannabis* plants they will of course be subject to a degree of variation in their composition. Generally the amounts by which each of the phytocannabinoid components will vary by will be in the range of ±10% (w/w). However depending on the starting plant material and the method of extraction used these amounts may vary by as little as ±5% up to ±50% (w/w).

TABLE 2.1.1

Cannabigerol BDS amount in total and range

| CBG BDS | Amount (% w/w) | Range (±10%) | Range (±25%) | Range (±50%) |
|---|---|---|---|---|
| CBGV | 0.33 | 0.30-0.36 | 0.25-0.41 | 0.17-0.50 |
| CBG | 66.96 | 60.3-73.7 | 50.2-83.7 | 33.5-100.0 |
| THC | 0.03 | 0.02-0.033 | 0.023-0.038 | 0.015-0.045 |
| CBC | 0.07 | 0.06-0.08 | 0.05-0.09 | 0.035-0.105 |
| CBG (related substance) | 1.35 | 1.22-1.49 | 1.01-1.69 | 0.68-2.03 |
| Total Cannabinoids | 68.74 | | | |
| Total Non-cannabinoids | 31.26 | | | |

The total phytocannabinoid containing fraction of CBG BDS comprises approximately 61-75% (w/w) of the total BDS.

TABLE 2.1.2

Cannabigerol BDS by percentage cannabinoid

| CBG BDS | Amount (% of total cannabinoid) |
|---|---|
| CBGV | 0.48 |
| CBG | 97.41 |
| THC | 0.04 |
| CBC | 0.10 |
| CBG (related substance) | 1.96 |

The amount of the principle phytocannabinoid in the CBG BDS as a percentage of the phytocannabinoid containing fraction is approximately 88-100% (w/w).

TABLE 2.2.1

Tetrahydrocannabinol BDS amount in total and range

| THC BDS | Amount (% w/w) | Range (±10%) | Range (±25%) | Range (±50%) |
|---|---|---|---|---|
| CBO | 0.2 | 0.18-0.22 | 0.15-0.25 | 0.1-0.3 |
| CBG | 2.0 | 1.8-2.2 | 1.5-2.5 | 1.0-3.0 |
| CBD | 1.0 | 0.9-1.1 | 0.75-1.25 | 0.5-1.5 |
| THCV | 1.1 | 0.99-1.21 | 0.83-1.38 | 0.55-1.65 |
| CBN | 3.0 | 2.7-3.3 | 2.25-3.75 | 1.5-4.5 |
| THC (related substances) | 0.6 | 0.54-0.66 | 0.45-0.75 | 0.3-0.9 |
| THC | 74.0 | 66.6-81.4 | 55.5-92.5 | 37.0-100.0 |
| CBC | 2.0 | 1.8-2.2 | 1.5-2.5 | 1.0-3.0 |
| THCA | 1.5 | 1.35-1.65 | 1.13-1.88 | 0.75-2.25 |
| Total Cannabinoids | 85.40 | | | |
| Total Non-cannabinoids | 14.60 | | | |

The total phytocannabinoid containing fraction of THC BDS comprises approximately 77-94% (w/w) of the total BDS.

TABLE 2.2.2

Tetrahydrocannabinol BDS by percentage cannabinoid

| THC BDS | Amount (% of total cannabinoid) |
|---|---|
| CBO | 0.23 |
| CBG | 2.34 |
| CBD | 1.17 |
| THCV | 1.29 |
| CBN | 3.51 |
| THC (related substances) | 0.70 |
| THC | 86.65 |
| CBC | 2.34 |
| THCA | 1.76 |

The amount of the principle phytocannabinoid in the THC BDS as a percentage of the phytocannabinoid containing fraction is approximately 78-95% (w/w).

TABLE 2.3.1

Cannabidiol BDS amount in total and range

| CBD BDS | Amount (% w/w) | Range (±10%) | Range (±25%) | Range (±50%) |
|---|---|---|---|---|
| CBD (related substances) | 0.3 | 0.27-0.33 | 0.23-0.38 | 0.15-0.45 |
| CBDV | 1.9 | 1.71-2.09 | 1.43-2.38 | 0.95-2.85 |
| CBDA | 1.3 | 1.17-1.43 | 0.98-1.63 | 0.65-1.95 |
| CBG | 2.5 | 2.25-2.75 | 1.88-3.13 | 1.25-3.75 |
| CBN | 0.2 | 0.18-0.22 | 0.15-0.25 | 0.1-0.3 |
| CBD | 70.0 | 63.0-77.0 | 52.5-87.5 | 35.0-100.0 |
| THC | 5.5 | 4.95-6.05 | 4.13-6.88 | 2.75-8.25 |
| CBC | 5.6 | 5.04-6.16 | 4.20-7.00 | 2.80-8.40 |
| Total Cannabinoids | 87.30 | | | |
| Total Non-cannabinoids | 12.70 | | | |

The total phytocannabinoid containing fraction of CBD BDS comprises approximately 79-96% (w/w) of the total BDS.

TABLE 2.3.2

Cannabidiol BDS by percentage cannabinoid

| CBD BDS | Amount (% of total cannabinoid) |
|---|---|
| CBD (related substances) | 0.34 |
| CBDV | 2.18 |
| CBDA | 1.49 |
| CBG | 2.86 |
| CBN | 0.23 |
| CBD | 80.18 |
| THC | 6.30 |
| CBC | 6.41 |

The amount of the principle phytocannabinoid in the CBD BDS as a percentage of the phytocannabinoid containing fraction is approximately 72-88% (w/w).

TABLE 2.4.1

Cannabichromene BDS amount in total and range

| CBC BDS | Amount (% w/w) | Range (±10%) | Range (±25%) | Range (±50%) |
|---|---|---|---|---|
| CBG | 0.91 | 0.82-1.00 | 0.68-1.14 | 0.46-1.37 |
| CBD | 3.96 | 3.56-4.36 | 2.97-4.95 | 1.98-5.94 |
| CBCV | 0.74 | 0.67-0.81 | 0.56-0.93 | 0.37-1.11 |
| THC | 1.76 | 1.58-1.94 | 1.32-2.20 | 0.88-2.64 |
| CBC (related substances) | 0.13 | 0.12-0.14 | 0.10-0.16 | 0.07-0.20 |
| CBC | 42.95 | 38.65-47.25 | 32.22-56.69 | 21.48-64.43 |
| CBCA | 0.56 | 0.50-0.62 | 0.42-0.70 | 0.28-0.84 |
| CBL | 3.54 | 3.19-3.89 | 2.67-4.43 | 1.77-5.31 |
| Total Cannabinoids | 54.55 | | | |
| Total Non-cannabinoids | 45.45 | | | |

The total phytocannabinoid containing fraction of CBC BDS comprises approximately 49-60% (w/w) of the total BDS.

TABLE 2.4.2

Cannabichromene BDS by percentage cannabinoid

| CBC BDS | Amount (% of total cannabinoid) |
|---|---|
| CBG | 1.67 |
| CBD | 7.26 |
| CBCV | 1.36 |
| THC | 3.23 |
| CBC (related substances) | 0.24 |
| CBC | 78.74 |
| CBCA | 1.03 |
| CBL | 6.49 |

The amount of the principle phytocannabinoid in the CBC BDS as a percentage of the phytocannabinoid containing fraction is approximately 71-87% (w/w). The CBC BDS also has two secondary cannabinoids: CBD which is present at approximately 6.5-8% (w/w) of the phytocannabinoid containing fraction and CBL which is present at approximately 5.8-7.1% (w/w) of the phytocannabinoid containing fraction.

TABLE 2.5.1

Tetrahydrocannabivarin BDS amount in total and range

| THCV BDS | Amount (% w/w) | Range (±10%) | Range (±25%) | Range (±50%) |
|---|---|---|---|---|
| CBGV | 0.15 | 0.14-0.17 | 0.11-0.19 | 0.07-0.23 |
| CBNV | 1.30 | 1.20-1.40 | 1.00-1.60 | 0.65-1.95 |
| THCV | 64.49 | 58.04-70.94 | 48.37-80.61 | 32.25-96.74 |
| CBCV | 0.65 | 0.59-0.72 | 0.49-0.81 | 0.33-0.98 |
| THC-C4 | 0.82 | 0.74-0.90 | 0.62-1.03 | 0.41-1.23 |
| CBN | 0.15 | 0.14-0.17 | 0.11-0.19 | 0.07-0.23 |
| THCVA | 0.36 | 0.32-0.40 | 0.27-0.45 | 0.18-0.54 |
| THC | 13.43 | 12.09-14.77 | 10.07-16.79 | 7.72-20.15 |
| Unknowns | 0.58 | 0.52-0.64 | 0.44-0.73 | 0.29-0.87 |
| Total Cannabinoids | 81.93 | | | |
| Total Non-cannabinoids | 18.07 | | | |

The total phytocannabinoid containing fraction of THCV BDS comprises approximately 74-90% (w/w) of the total BDS.

TABLE 2.5.2

Tetrahydrocannabivarin BDS by percentage cannabinoid

| THCV BDS | Amount (% of total cannabinoid) |
|---|---|
| CBGV | 0.18 |
| CBNV | 1.59 |
| THCV | 78.71 |
| CBCV | 0.79 |
| THC-C4 | 1.00 |
| CBN | 0.18 |
| THCVA | 0.44 |
| THC | 16.39 |
| Unknowns | 0.71 |

The amount of the principle phytocannabinoid in the THCV BDS as a percentage of the phytocannabinoid containing fraction is approximately 71-87% (w/w). The THCV BDS also has a secondary cannabinoid THC which is present at approximately 14.8-18% (w/w) of the phytocannabinoid containing fraction.

TABLE 2.6.1

Cannabidivarin BDS amount in total and range

| CBDV BDS | Amount (% w/w) | Range (±10%) | Range (±25%) | Range (±50%) |
|---|---|---|---|---|
| CBDVA | 0.14 | 0.13-0.15 | 0.11-0.18 | 0.07-0.21 |
| CBDV | 41.19 | 37.07-45.31 | 30.89-51.49 | 20.60-61.79 |
| CBDA | 0.07 | 0.06-0.08 | 0.05-0.09 | 0.04-0.11 |
| CBG | 0.59 | 0.53-0.65 | 0.44-0.74 | 0.30-0.89 |
| CBD | 17.70 | 15.93-19.47 | 13.28-22.13 | 8.85-26.55 |
| THCV | 3.06 | 2.75-6.12 | 2.30-3.83 | 1.53-4.59 |
| CBCV | 4.35 | 3.92-4.79 | 3.26-5.44 | 2.18-6.53 |
| THC | 0.88 | 0.79-0.97 | 0.66-1.10 | 0.44-1.32 |
| CBDV (related substances) | 2.20 | 1.98-2.42 | 1.65-2.75 | 1.10-3.30 |
| CBC | 0.93 | 0.84-1.02 | 0.70-1.16 | 0.47-1.40 |
| Total Cannabinoids | 71.11 | | | |
| Total Non-cannabinoids | 28.89 | | | |

The total phytocannabinoid containing fraction of CBDV BDS comprises approximately 64-78% (w/w) of the total BDS.

TABLE 2.6.2

Cannabidivarin BDS by percentage cannabinoid

| CBDV BDS | Amount (% of total cannabinoid) |
|---|---|
| CBDVA | 0.20 |
| CBDV | 57.92 |
| CBDA | 0.10 |
| CBG | 0.83 |
| CBD | 24.89 |
| THCV | 4.30 |
| CBCV | 6.12 |
| THC | 1.24 |
| CBDV (related substances) | 3.09 |
| CBC | 1.31 |

The amount of the principle phytocannabinoid in the CBDV BDS as a percentage of the phytocannabinoid containing fraction is approximately 52-64% (w/w). The CBDV BDS also has two secondary cannabinoids: CBD which is present at approximately 22.4-27.4% (w/w) of the phytocannabinoid containing fraction and CBCV which is present at approximately 5.5-6.7% (w/w) of the phytocannabinoid containing fraction.

TABLE 2.7.1

Cannabigerol propyl variant BDS amount in total and range

| CBGV BDS | Amount (% w/w) | Range (±10%) | Range (±25%) | Range (±50%) |
|---|---|---|---|---|
| CBGV | 45.92 | 41.33-50.51 | 34.44-57.40 | 22.96-68.88 |
| CBG | 12.79 | 11.51-14.07 | 9.59-15.99 | 6.40-19.19 |
| THC | 0.08 | 0.07-0.09 | 0.06-0.10 | 0.04-0.12 |
| CBC | 0.21 | 0.19-0.23 | 0.16-0.25 | 0.11-0.32 |
| CBG (related substances) | 1.45 | 1.31-1.60 | 1.09-1.81 | 0.73-2.18 |
| Total Cannabinoids | 60.45 | | | |
| Total Non-cannabinoids | 39.55 | | | |

The total phytocannabinoid containing fraction of CBGV BDS comprises approximately 54-66% (w/w) of the total BDS.

TABLE 2.7.2

Cannabigerol propyl variant BDS by percentage cannabinoid

| CBGV BDS | Amount (% of total cannabinoid) |
|---|---|
| CBGV | 75.96 |
| CBG | 21.16 |
| THC | 0.13 |
| CBC | 0.35 |
| CBG (related substances) | 2.40 |

The amount of the principle phytocannabinoid in the CBGV BDS as a percentage of the phytocannabinoid containing fraction is approximately 68-84% (w/w). The CBGV BDS also has a secondary cannabinoid CBG which is present at approximately 19-23% (w/w) of the phytocannabinoid containing fraction.

Table 2.8.1

Tetrahydrocannabinolic acid BDS amount in total and range

| THCA BDS | Amount (% w/w) | Range (±10%) | Range (±25%) | Range (±50%) |
|---|---|---|---|---|
| CBO | 0.06 | 0.05-0.07 | 0.05-0.08 | 0.03-0.09 |
| CBG | 1.91 | 1.72-2.10 | 1.43-2.39 | 0.96-2.87 |
| CBD | 0.30 | 0.27-0.33 | 0.23-0.38 | 0.15-0.45 |
| THC (related substances) | 0.16 | 0.14-0.18 | 0.12-0.20 | 0.08-0.24 |
| THCV | 0.05 | 0.04-0.06 | 0.04-0.06 | 0.03-0.08 |
| CBN | 1.11 | 1.00-1.22 | 0.83-1.39 | 0.56-1.67 |
| THC | 8.93 | 8.04-9.82 | 6.70-11.16 | 4.47-13.40 |
| CBL | 0.17 | 0.15-0.19 | 0.13-0.21 | 0.09-0.26 |
| CBC | 0.26 | 0.23-0.29 | 0.20-0.33 | 0.13-0.39 |
| THCA | 46.98 | 42.28-51.68 | 35.24-58.73 | 23.49-70.47 |
| Total Cannabinoids | 59.93 | | | |
| Total Non-cannabinoids | 40.07 | | | |

The total phytocannabinoid containing fraction of THCA BDS comprises approximately 54-66% (w/w) of the total BDS.

TABLE 2.8.2

Tetrahydrocannabinolic acid
BDS by percentage cannabinoid

| THCA BDS | Amount (% of total cannabinoid) |
|---|---|
| CBO | 0.10 |
| CBG | 3.19 |
| CBD | 0.50 |
| THC (related substances) | 0.27 |
| THCV | 0.08 |
| CBN | 1.85 |
| THC | 14.90 |
| CBL | 0.28 |
| CBC | 0.43 |
| THCA | 78.39 |

The amount of the principle phytocannabinoid in the THCA BDS as a percentage of the phytocannabinoid containing fraction is approximately 71-86% (w/w). The THCA BDS also has a secondary cannabinoid THC which is present at approximately 13.4-16.4% (w/w) of the phytocannabinoid containing fraction.

TABLE 2.9.1

Cannabidiolic acid BDS amount in total and range

| CBDA BDS | Amount (% w/w) | Range (±10%) | Range (±25%) | Range (±50%) |
|---|---|---|---|---|
| CBDV | 0.23 | 0.21-0.25 | 0.17-0.29 | 0.12-0.37 |
| CBDA | 68.14 | 61.33-74.95 | 51.11-85.18 | 34.07-100.0 |
| CBD | 5.36 | 4.82-5.90 | 4.02-6.70 | 2.68-8.04 |
| CBN | 0.19 | 0.17-0.21 | 0.14-0.24 | 0.1-0.29 |
| THC | 0.53 | 0.48-0.58 | 0.40-0.66 | 0.27-0.80 |
| CBL | 0.29 | 0.26-0.32 | 0.22-0.36 | 0.15-0.44 |
| CBC | 0.38 | 0.34-0.42 | 0.29-0.48 | 0.19-0.57 |
| CBD (related substances) | 3.31 | 2.98-3.64 | 2.48-4.14 | 1.66-4.98 |
| Total Cannabinoids | 78.43 | | | |
| Total Non-cannabinoids | 21.57 | | | |

The total phytocannabinoid containing fraction of CBDA BDS comprises approximately 71-86% (w/w) of the total BDS.

TABLE 2.9.2

Cannabidiolic acid BDS by percentage cannabinoid

| CBDA BDS | Amount (% of total cannabinoid) |
|---|---|
| CBDV | 0.29 |
| CBDA | 86.88 |
| CBD | 6.83 |
| CBN | 0.24 |
| THC | 0.68 |
| CBL | 0.37 |
| CBC | 0.48 |
| CBD (related substances) | 4.22 |

The amount of the principle phytocannabinoid in the CBDA BDS as a percentage of the phytocannabinoid containing fraction is approximately 78-96% (w/w). The CBDA BDS also has a secondary cannabinoid CBD which is present at approximately 6.1-7.5% (w/w) of the phytocannabinoid containing fraction.

TABLE 2.10.1

Tetrahydrocannabivarinic acid BDS amount in total and range

| THCVA BDS | Amount (% w/w) | Range (±10%) | Range (±25%) | Range (±50%) |
|---|---|---|---|---|
| CBDVA | 1.44 | 1.30-1.58 | 1.08-1.80 | 0.72-2.16 |
| CBNV | 0.35 | 0.32-0.39 | 0.26-0.44 | 0.18-0.53 |
| THCV | 13.17 | 11.85-14.49 | 9.88-16.46 | 6.59-19.76 |
| CBCV | 1.97 | 1.77-2.17 | 1.48-2.46 | 0.99-2.96 |
| THC-C4 | 0.36 | 0.32-0.40 | 0.27-0.45 | 0.18-0.54 |
| THCVA | 40.61 | 36.55-44.67 | 30.46-50.76 | 20.31-50.76 |
| THC | 3.53 | 3.18-3.88 | 2.65-4.41 | 1.77-5.30 |
| CBC | 0.20 | 0.18-0.22 | 0.15-0.25 | 0.1-0.3 |
| THCA | 6.29 | 5.66-6.92 | 4.72-7.86 | 3.15-9.44 |
| Unknowns | 0.45 | 0.41-0.50 | 0.38-0.56 | 0.23-0.68 |
| Total Cannabinoids | 68.37 | | | |
| Total Non-cannabinoids | 31.63 | | | |

The total phytocannabinoid containing fraction of THCVA BDS comprises approximately 37-45% (w/w) of the total BDS.

Table 2.10.2

Tetrahydrocannabivarinic acid BDS by percentage cannabinoid

| THCVA BDS | Amount (% of total cannabinoid) |
|---|---|
| CBDVA | 2.11 |
| CBNV | 0.51 |
| THCV | 19.26 |
| CBCV | 2.88 |
| THC-C4 | 0.53 |
| THCVA | 59.40 |
| THC | 4.90 |
| CBC | 0.29 |
| THCA | 9.20 |
| Unknowns | 0.66 |

The amount of the principle phytocannabinoid in the THCVA BDS as a percentage of the phytocannabinoid containing fraction is approximately 53-65% (w/w). The THCVA BDS also a secondary cannabinoid THCV which is present at approximately 17.3-21.2% (w/w) of the phytocannabinoid containing fraction.

The following table details an overview of the amount of cannabinoid and non-cannabinoid fraction in each cannabinoid BDS and the amount of cannabinoid as a percentage of the total cannabinoids in each BDS. As previously discussed the skilled person will appreciate that these values will vary due to the naturally occurring nature of the starting plant material.

TABLE 2.11.1

Overview of cannabinoid BDS

| BDS | Cannabinoid Fraction (% w/w) | Non-cannabinoid Fraction (% w/w) | Amount of principle cannabinoid (% of total cannabinoid) |
|---|---|---|---|
| CBG | 68.7 | 31.3 | 97.4 |
| THC | 85.4 | 14.6 | 86.7 |
| CBD | 87.3 | 12.7 | 80.2 |
| CBC | 54.5 | 45.5 | 78.7 |
| THCV | 81.9 | 18.1 | 78.7 |
| CBDV | 71.1 | 28.9 | 57.9 |

TABLE 2.11.1-continued

Overview of cannabinoid BDS

| BDS | Cannabinoid Fraction (% w/w) | Non-cannabinoid Fraction (% w/w) | Amount of principle cannabinoid (% of total cannabinoid) |
|---|---|---|---|
| CBGV | 60.5 | 39.5 | 76.0 |
| THCA | 59.9 | 40.1 | 78.4 |
| CBDA | 78.4 | 21.6 | 86.9 |
| THCVA | 68.4 | 31.6 | 59.4 |

It is desirable to maximise the amount of principle phytocannabinoid in the phytocannabinoid containing fraction, however in some cases synergy may exist between the principle and secondary cannabinoids which may lead to enhanced medicinal effects.

It is also desirable for the range by which the percentage of the phytocannabinoid containing fraction, the non-phytocannabinoid containing fraction and the amount of principle phytocannabinoid varies. In most cases this variation will be small and be in the range of ±5%, up to ±10%, up to ±25% and preferably no greater than ±50%.

The non-cannabinoid components of a phytocannabinoid BDS may play an important role in the BDS's pharmacology. As such the terpene profile is classified below. The following tables illustrate the terpene profile of a CBD chemovar which is representative of a high phytocannabinoid containing plant. Five plants were freshly harvested and extracted using steam distillation. The principle monoterpene and sesquiterpene are highlighted in bold.

TABLE 2.12.1

Monoterpene amount by percentage of total terpene fraction and ranges

| Monoterpenes | Amount (% of terpene fraction) | Range (±10%) | Range (±25%) | Range (±50%) |
|---|---|---|---|---|
| Pinene (alpha & beta) | 10.56 | 9.50-11.62 | 7.92-13.20 | 5.28-15.84 |
| Myrcene | 39.46 | 35.51-43.41 | 29.60-49.33 | 19.73-59.19 |
| Limonene | 4.14 | 3.73-4.55 | 3.11-5.18 | 2.07-6.21 |
| Beta-ocimene | 4.04 | 3.64-4.44 | 3.03-5.05 | 2.02-6.06 |
| Total | 58.20 | | | |

The monoterpene containing fraction comprises approximately 52-64% (w/w) of the total terpene fraction.

TABLE 2.12.2

Monoterpene amount by percentage of monoterpenes

| Monoterpenes | Amount (% of monoterpene fraction) |
|---|---|
| Pinene (alpha & beta) | 18.14 |
| Myrcene | 67.80 |
| Limonene | 7.12 |
| Beta-ocimene | 6.94 |

The amount of the principle monoterpene myrcene in the monoterpene fraction as a percentage of the monoterpene fraction is approximately 61-75% (w/w). The monoterpene fraction also has a secondary monoterpene pinene which is present at approximately 16.3-20% (w/w) of the monoterpene fraction.

TABLE 2.12.3

Sesquiterpene amount by percentage of total terpene fraction and ranges

| Sesquiterpenes | Amount (% of terpene fraction) | Range (±10%) | Range (±25%) | Range (±50%) |
|---|---|---|---|---|
| Caryophyllenes (t & oxide) | 29.27 | 26.34-32.20 | 21.95-36.59 | 14.64-43.91 |
| Bergotamene | 0.18 | 0.16-0.20 | 0.14-0.23 | 0.09-0.27 |
| Humulene | 7.97 | 7.17-8.77 | 5.98-9.96 | 3.99-11.96 |
| Aromadendrene | 0.33 | 0.30-0.36 | 0.25-0.41 | 0.17-0.50 |
| Selinene | 0.59 | 0.53-0.65 | 0.44-0.74 | 0.30-0.89 |
| Anon | 0.44 | 0.40-0.48 | 0.33-0.55 | 0.22-0.66 |
| Farnesene (Z,E & alpha) | 1.55 | 1.40-1.71 | 1.16-1.94 | 0.78-2.33 |
| alpha Gurjunene | 0.12 | 0.11-0.13 | 0.09-0.15 | 0.06-0.18 |
| Bisabolene | 0.39 | 0.35-0.43 | 0.29-0.49 | 0.20-0.59 |
| Nerolidol | 0.43 | 0.39-0.47 | 0.32-0.54 | 0.22-0.65 |
| Diepicedrene-1-oxide | 0.38 | 0.34-0.42 | 0.29-0.48 | 0.19-0.57 |
| Alpha-Bisabolol | 0.16 | 0.14-0.18 | 0.12-0.20 | 0.08-0.24 |
| Total | 41.80 | | | |

The sesquiterpene containing fraction comprises approximately 27-32% (w/w) of the total terpene fraction.

TABLE 2.12.4

Sesquiterpene amount by percentage of sesquiterpenes

| Sesquiterpenes | Amount (% of sesquiterpene fraction) |
|---|---|
| Caryophyllenes (t & oxide) | 70.02 |
| Bergotamene | 0.43 |
| Humulene | 19.07 |
| Aromadendrene | 0.79 |
| Selinene | 1.41 |
| Anon | 1.05 |
| Farnesene (Z,E & alpha) | 3.71 |
| alpha Gurjunene | 0.29 |
| Bisabolene | 0.93 |
| Nerolidol | 1.03 |
| Diepicedrene-1-oxide | 0.91 |
| Alpha-Bisabolol | 0.38 |

Patent application number PCT/GB2008/001837 describes the production of a 'zero cannabinoid' plant. These plants were produced by selective breeding to produce a *Cannabis sativa* L plant that contained a generally qualitatively similar terpene profile as a *Cannabis sativa* L plant that produced cannabinoids yet it was devoid of any cannabinoids. These plants can be used to produce cannabinoid-free plant extracts which are useful control plants in experiments and clinical trials. A breakdown of the terpene profile produced in the plants can be found in the table below. The primary monoterpenes and sesquiterpene are highlighted in bold.

TABLE 2.13.1

Monoterpene amount by percentage of total terpene fraction and ranges

| Monoterpenes | Amount (% of terpene fraction) | Range (±10%) | Range (±25%) | Range (±50%) |
|---|---|---|---|---|
| Pinene (alpha & beta) | 29.34 | 26.41-32.27 | 22.01-36.68 | 14.67-44.01 |
| Myrcene | 29.26 | 26.33-32.19 | 21.95-36.58 | 14.63-43.89 |
| Limonene | 5.32 | 4.79-5.85 | 3.99-6.65 | 2.66-7.98 |
| Linalol | 4.50 | 4.05-4.95 | 3.38-5.63 | 2.25-6.75 |
| Verbenol (cis & trans) | 3.45 | 3.11-3.80 | 2.59-4.31 | 1.73-5.18 |
| Total | 71.87 | | | |

The monoterpene containing fraction comprises approximately 65-79% (w/w) of the total terpene fraction.

TABLE 2.13.2

Monoterpene amount by percentage of monoterpenes

| Monoterpenes | Amount (% of monoterpene fraction) |
|---|---|
| Pinene (alpha & beta) | 40.82 |
| Myrcene | 40.71 |
| Limonene | 7.41 |
| Linalol | 6.26 |

The zero cannabinoid plant was found to comprise two principle monoterpenes; pinene and myrcene. The amount of the principle monoterpene myrcene in the monoterpene fraction as a percentage of the monoterpene fraction is approximately 37-45% (w/w). The amount of the principle monoterpene pinene in the monoterpene fraction as a percentage of the monoterpene fraction is approximately 37-45% (w/w).

TABLE 2.13.3

Sesquiterpene amount by percentage of total terpene fraction and ranges

| Sesquiterpenes | Amount (% of terpene fraction) | Range (±10%) | Range (±25%) | Range (±50%) |
|---|---|---|---|---|
| Caryophyllenes (t & oxide) | 10.89 | 9.80-11.98 | 8.17-13.61 | 5.45-16.34 |
| Bergotamene | 2.51 | 2.26-2.76 | 1.88-3.14 | 1.26-3.77 |
| Farnesene (Z, E & alpha) | 3.43 | 3.09-3.77 | 2.57-4.29 | 1.72-5.15 |
| Humulene (& epoxide II) | 5.04 | 4.54-5.54 | 3.78-6.30 | 2.52-7.56 |
| delta guaiene | 2.40 | 2.16-2.64 | 1.80-3.00 | 1.20-3.60 |
| Bisabolene | 3.85 | 3.47-4.24 | 2.89-4.81 | 1.93-5.78 |
| Total | 28.12 | | | |

The sesquiterpene containing fraction comprises approximately 25-31% (w/w) of the total terpene fraction.

TABLE 2.12.4

Sesquiterpene amount by percentage of sesquiterpenes

| Sesquiterpenes | Amount (% of sesquiterpene fraction) |
|---|---|
| Caryophyllenes (t & oxide) | 38.73 |
| Bergotamene | 8.93 |
| Farnesene (Z, E & alpha) | 12.20 |
| Humulene (& epoxide II) | 17.92 |
| delta guaiene | 8.53 |
| Bisabolene | 13.69 |

The amount of the principle sesquiterpene caryophylene in the sesquiterpene fraction as a percentage of the sesquiterpene fraction is approximately 35-43% (w/w). The sesquiterpene fraction also has a secondary sesquiterpene humulene which is present at approximately 16-20% (w/w) of the sesquiterpene fraction.

Example 3

Effect of Phytocannabinoids on Apoptosis in Hormone-Insensitive Prostate Cancer Cell Line (DU-145) and Hormone-Sensitive Prostate Cancer Cell Line (LNCaP)

Figure 2:
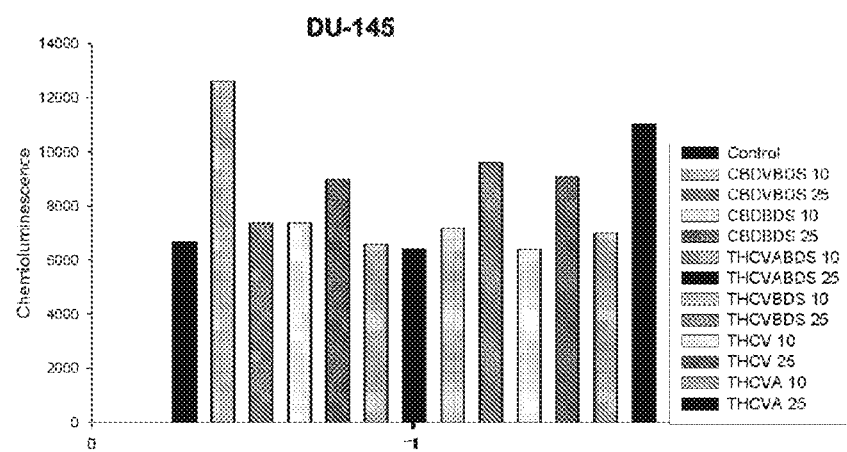
FIG. 2 shows the effect of cannabinoids on apoptosis in hormone-insensitive prostate cancer cell line (DU-145) and hormone-sensitive prostate cancer cell line (LNCaP)
Figure 2:
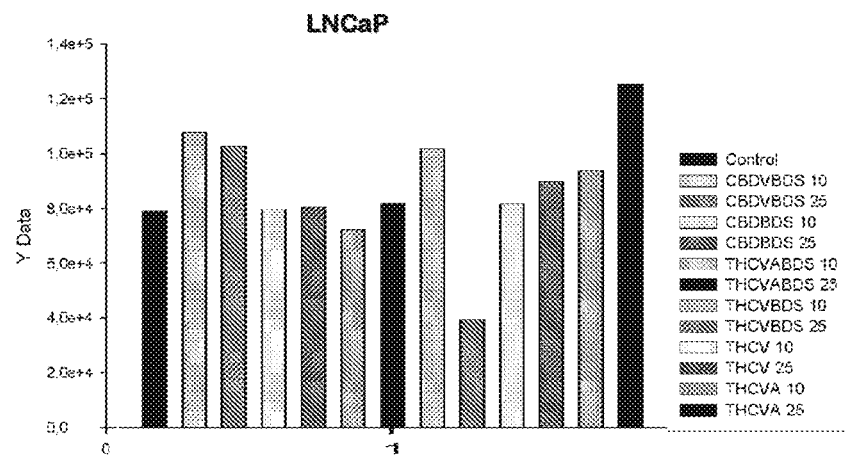

The effect of CBDV BDS, CBD BDS, THCVA BDS, THCV BDS, isolated THCV and isolated THCVA on the apoptosis of two prostate cancer cell lines were tested using a chemiluminescence assay for caspase 3/7 release. Two different concentrations of cannabinoids were tested; a low dose (10 µM) and a high dose (25 µM). The chemiluminescence that were recorded for each phytocannabinoid are detailed in FIG. 2.

In the hormone-insensitive prostate cancer cell line (DU-145) the highest chemiluminescence and as such the highest pro-apoptotic effects were found with the low dose CBDV BDS and the high dose isolated THCVA purified cannabinoid at 25 µM. The high dose THCV BDS, CBD BDS and isolated THCV also showed apotosis levels over that of the control.

In the hormone-sensitive prostate cancer cell line (LNCaP) the highest chemiluminescence and as such the highest pro-apoptotic effect was found with the high dose isolated THCVA. The low and high dose CBDV BDS were also shown to have apoptotic effects on the cancer cells.

These data infer that both the phytocannabinoid BDS's and isolated phytocannabinoid may be useful in the treatment of cancer as they are able to exert an apoptotic effect on cancer cells.

Example 4

Effect of Phytocannabinoids on the G-Protein Coupled Receptor GPR55

An ERK Alphascreen assay was undertaken using GPR55-HEK cells. The different cannabinoids tested displayed different pharmacological profiles at GPR55 as is illustrated in Table 4.1 below.

TABLE 4.1

Effect of phytocannabinoids at GPR55

| Compound | Effect at GPR55 |
|---|---|
| CBD (control) | Antagonist |
| THCV | Antagonist (at low concentrations) |
| CBGA | Inverse agonist |
| CBGV | Antagonist |
| CBDA | Antagonist |
| CBDV | Antagonist |

A significant reduction in the ERK signalling pathway has been shown to lead to induction of apotosis (Chang et al., 2003).

These data suggest that GPR55 expression by cancer cells can be antagonised by all the phytocannabinoids tested making them good target compounds for use in the treatment of cancer.

Example 5

Effect of Phytocannabinoids on Inhibition of Monoacylglyceride Lipase (MAGL) and Diacylglyceride Lipase (DAGL)

The effects of the phytocannabinoid BDS THCA, CBN, CBGA, CBDA and CBCV were tested to determine whether they were able to inhibit the MAGL and DAGL enzymes which are able to hydrolyse the endogenous cannabinoid 2-AG to arachidonic acid and glycerol. The results generated from these experiments are detailed in Table 5.1 below.

TABLE 5.1

Effect of phytocannabinoids on inhibition of monoacylglyceride lipase (MAGL) and diacylglyceride lipase (DAGL)

| Sample | MAG $IC_{50}$ | Max concentration tested (% inhibition) | DAGL $IC_{50}$ | Max concentration tested (% inhibition) |
|---|---|---|---|---|
| THCA | 46 µM | 100 µM (81.9%) | 25 µM | 50 µM (79.3%) |
| CBN | >50 µM | 50 µM (31.5%) | >50 µM | 50 µM (26.9%) |
| CBGA | >50 µM | 50 µM (17.2%) | 30 µM | 100 µM (67.5%) |
| CBDA | >50 µM | 50 µM (18.5%) | 23 µM | 100 µM (91.4%) |
| CBCV | >50 µM | 50 µM (4.8%) | >50 µM | 50 µM (18.9%) |

As can be seen the phytocannabinoid THCA was most effective at inhibiting DAGL and the all the phytocannabinoid acids (THCA, CBDA and CBGA) were effective at inhibiting MAGL. These data infer that these phytocannabinoid might be useful in the treatment of cancer as they are able to prevent the endogenous cannabinoid 2-AG from being hydrolysed and as such may prevent cancerous cell formation.

An additional experiment was undertaken to determine whether phytocannabinoid BDS were more effective at inhibition of MAGL than their respective purified counterparts. For this experiment CBG BDS was used as this BDS was the easiest to purify and reconstitute. Four different test articles were used: CBG BDS, isolated CBG, CBG-free CBG BDS and CBG reconstituted BDS, whereby the CBG-free BDS (as prepared in Example 1) was spiked with isolated CBG at the same concentration of CBG as CBG BDS. Table 5.2 below details the data obtained.

TABLE 5.2

Effect of BDS, purified compounds and reconstituted BDS on inhibition of monoacylglyceride lipase (MAGL)

| SAMPLE | EC50 on MAGL | Max tested on MAGL % inhibition |
|---|---|---|
| Isolated CBG | 195.2 µM | 100 µM (31.49%) |
| CBG BDS | 64.33 µM | 100 µM (57.93%) |
| CBG-Free BDS | 187.0 µM | 100 µM (36.55%) |
| Reconstituted CBG BDS | 70.28 µM | 100 µM (59.31%) |

As can be seen in Table 5.2 above the CBG BDS is of a similar potency as the reconstituted BDS. These data demonstrate a synergistic effect between the principle phytocannabinoid and the rest of the cannabinoid and non-cannabinoid components in the BDS.

These data infer that the use of phytocannabinoid BDS's comprising a non-cannabinoid component would be more efficacious in the treatment of cancer than isolated phytocannabinoids.

Example 6

Figure 3:
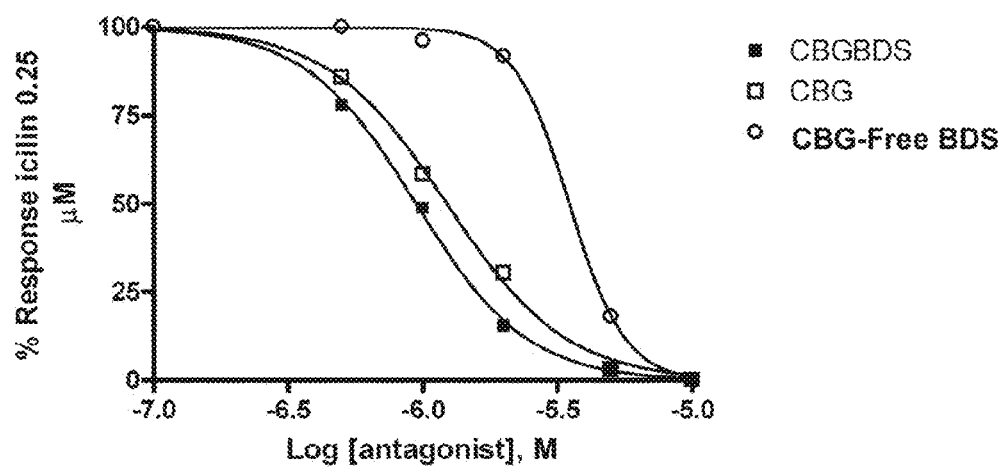
FIG. 3 shows the effect of cannabinoid BDS real and reconstituted on TRPM8 antagonism.
Figure 3:
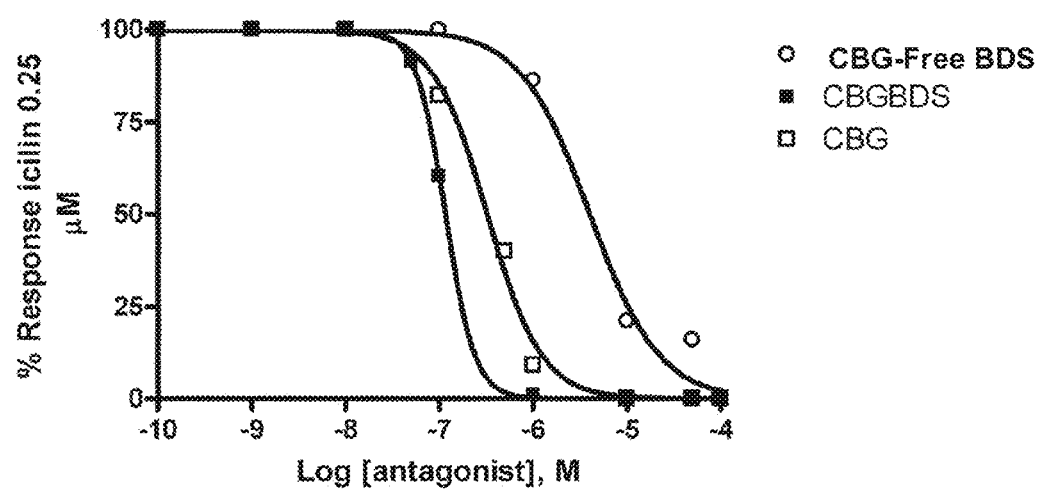

Effect of Phytocannabinoid BDS and Reconstituted Phytocannabinoid BDS on TRPM8 Antagonism The CBG BDS and the reconstituted CBG BDS as described in Example 5 above were used to determine their effectiveness on TRPM8 antagonism. Also tested for completeness were CBG-free BDS and purified CBG. The percentage response against 0.25 µM icilin were observed and are as detailed in FIG. 3.

As can be seen both CBG BDS and reconstituted CBG BDS gave a much higher response rate than either isolated CBG or the CBG-free BDS. These data again demonstrate the synergy between the principle phytocannabinoid and the other components in the BDS.

These data surmise that the use of a phytocannabinoid BDS would be a more effective treatment option in cancer.

Example 7

Effect of Phytocannabinoids in Hormone-Insensitive Prostate Cancer Cell Line (DU-145) and Hormone-Sensitive Prostate Cancer Cell Line (LNCaP) on Cell Vitality (MTT Assay)

Cells were seeded in presence of FBS in 6 wells multiwell with a density of $8 \times 10^4$ cells/well (DU-145) or $1 \times 10^5$ cells/well (LNCaP). After 7 hours, cells were starved of dihydrotestosterone (DHT) for 15 hours and treated with increased concentrations of compounds for 24 or 48 hours (absence of serum was maintained during the treatments). Cell viability was assessed by MTT staining.

Phytocannabinoid BDS and their respective isolated phytocannabinoids were tested in both the hormone-insensitive (DU-145) prostate cancer cells and hormone-sensitive (LNCaP) prostate cancer cells. Three different phytocannabinoids were chosen for this experiment: CBG BDS and isolated compound, CBC BDS and isolated compound and CBD BDS and isolated compound.

Table 7.1 details the data observed in the starved cells. As can be seen in each case the BDS has much more of an effect on the vitality of the prostate cancer cells than its respective isolated phytocannabinoid.

TABLE 7.1

Effect of phytocannabinoid BDS on cell vitality
(MTT Assay) — cells starved of dihydrotestosterone (DHT)

|  | DU-145 $IC_{50}$ on cell vitality | | LNCaP $IC_{50}$ on cell vitality | |
| --- | --- | --- | --- | --- |
| Sample | 24 h | 48 h | 24 h | 48 h |
| CBG | 11.8 μM | 5.8 μM | 10.8 μM | 8.1 μM |
| CBG BDS | 5.3 μM | 4.8 μM | 7.0 μM | 4.7 μM |
| CBC | 7.5 μM | 5.6 μM | 10.8 μM | 6.0 μM |
| CBC BDS | 4.9 μM | 4.5 μM | 6.3 μM | 5.3 μM |
| CBD | 5.5 μM | 4.9 μM | 5.3 μM | 5.6 μM |
| CBD BDS | 5.0 μM | 3.6 μM | 5.5 μM | 4.3 μM |

The experiment was repeated in the hormone-insensitive (DU-145) prostate cancer cells and hormone-sensitive (LNCaP) prostate cancer cells that had not been starved of DHT. Here just the CBG BDS and isolated CBG are illustrated in Table 7.2 below.

TABLE 7.2

Effect of CBG & CBG BDS on cell vitality
(MTT Assay) - non-DHT-starved Cells

| Sample | LNCaP $IC_{50}$ on cell vitality |
| --- | --- |
| CBG | >25 μM |
| CBG-BDS | 21.2 μM |

| Sample | DU-145 $IC_{50}$ on cell vitality |
| --- | --- |
| CBG | >25 μM |
| CBG-BDS | 24 μM |

As is demonstrated in Table 7.2 above the presence of DHT in the non-starved cells dramatically alters the effectiveness of the phytocannabinoid BDS and the isolated phytocannabinoids.

The data described above again illustrates that the phytocannabinoid BDS are more efficacious and as such a better compound to use in the treatment of cancer.

Example 8

Effect of Phytocannabinoids Alone or in Combination with a Chemotherapeutic Agent or an Anti-Androgen in Hormone-Insensitive Prostate Cancer Cell Line (DU-145) and Hormone-Sensitive Prostate Cancer Cell Line (LNCaP) in a Subcutaneous Xenograft Model The phytocannabinoids CBG BDS and CBD BDS were used in this experiment to demonstrate the in vivo effectiveness of the phytocannabinoid BDS's.

Cancer cells were maintained in vitro in an appropriate culture medium and were harvested, washed in culture medium and re-suspended in matrigel for ready for in vivo administration. 1-2×10$^7$ cells in 200 μl were injected subcutaneously into the left flank of mice. The mice were anaesthetised and a 0.5 mg 5-alpha-dihydrotestosterone pellet (21-day release) implanted subcutaneously into the scruff of each mouse to encourage tumour growth, and the wound was closed.

Once the implanted tumour volume reached between 100-200 mm (2-3 weeks) mice were allocated to their treatment groups. Treatment commenced on Day 17. The phytocannabinoid BDS was administered i.p. once daily at doses of 1, 10 & 100 mg/kg cannabinoid BDS for a further 25 days.

In a further experiment the chemotherapeutic agent taxotere (5 mg/kg) i.v. was administered weekly, alone or in combination with 100 mg/kg phytocannabinoid BDS.

The chemotherapeutic agent taxotere was used to exemplify the taxane drug class which are mitotic inhibitors.

In a further experiment CBD BDS at 100 mg/kg of CBD was evaluated for its action in combination with either 25 or 50 mg/kg of the anti-androgen bicalutamide.

The anti-androgen bicalutamide is an example of a hormone therapy drug used in the treatment of prostate cancer. Hormonal therapies interfere with the production of particular hormones by the body. Prostate cancer (when it is in the hormone sensitive stage) requires the male hormone testosterone (androgen) in order to grow. The prostate cancer cells have receptors on their surface which when the hormone attaches to it allows the cancer cell to grow.

The anti-androgen bicalutamide is structurally similar to testosterone and prevents the testosterone from binding to the cancer cell. Without the testosterone the cancer cells grow more slowly or may stop growing completely and as such the tumour may shrink as a result.

Mice were evaluated daily by an experienced technician for 4-5 weeks. Tumour dimensions were recorded at day 7 (caliper measurement of length and width and tumour cross-sectional area and volume calculated) and recorded three times weekly and body weight measured weekly.

The human dose equivalent (HED) can be estimated using the following formula:

$$HED = \text{Animal dose (mg/kg) multiplied by Animal } K_m \overline{\text{Human} K_m}$$

The $K_m$ for a mouse is 3 and the $K_m$ for a human is 37.

FIGS. 4A-4D detail the mean tumour volume and weight recorded in these experiments.

Figure 4A:
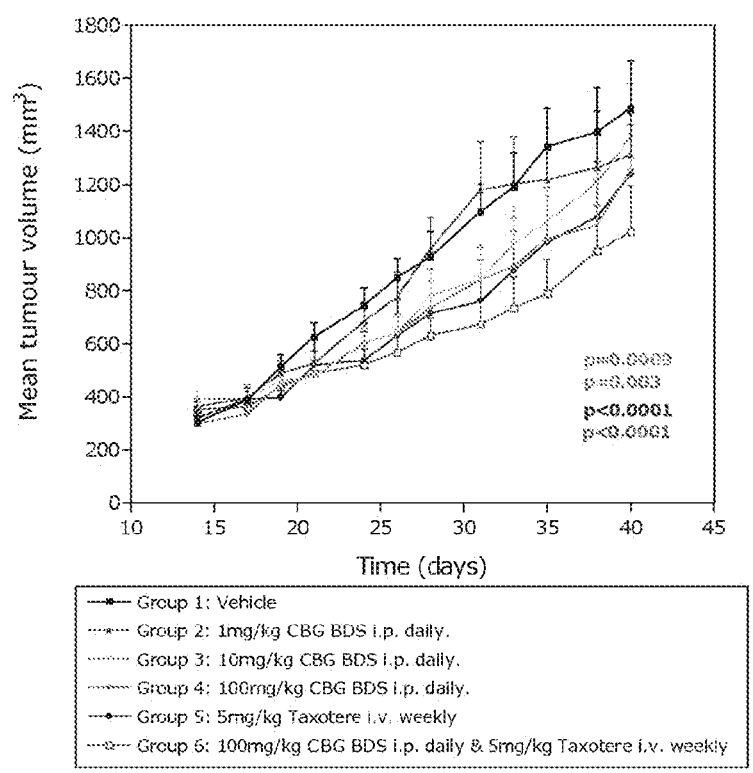

FIG. 4A shows that the growth rate of the tumour was inhibited in a dose dependant manner by CBG BDS. Both the 10 and 100 mg/kg doses of BDS were significant when compared to the vehicle group. In addition taxotere significantly inhibited both growth rate and terminal tumour volume, with a slight synergistic effect detected in the group treated with both CBG BDS and taxotere.

Figure 4B:
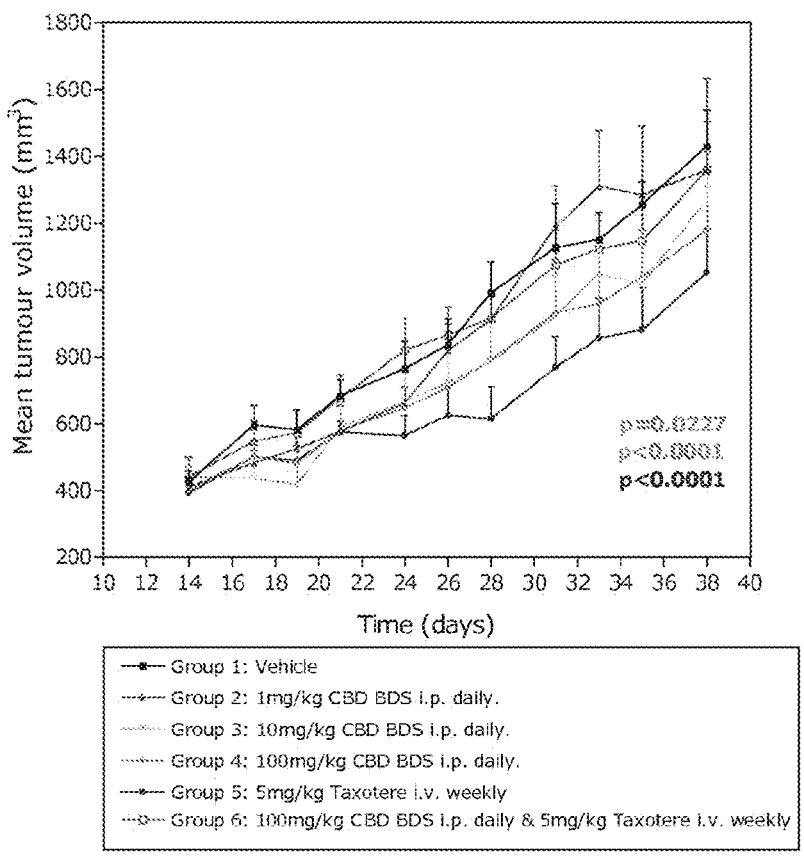

FIG. 4B shows that the growth rate of the tumour was inhibited in a dose dependant manner by CBD BDS. Both the 10 and 100 mg/kg doses of BDS were significant when compared to the vehicle group. Similarly to the experiments with CBG BDS the taxotere significantly inhibited both growth rate and terminal tumour volume, with a slight synergistic effect detected in the group treated with both CBD BDS and taxotere.

Figure 4D:
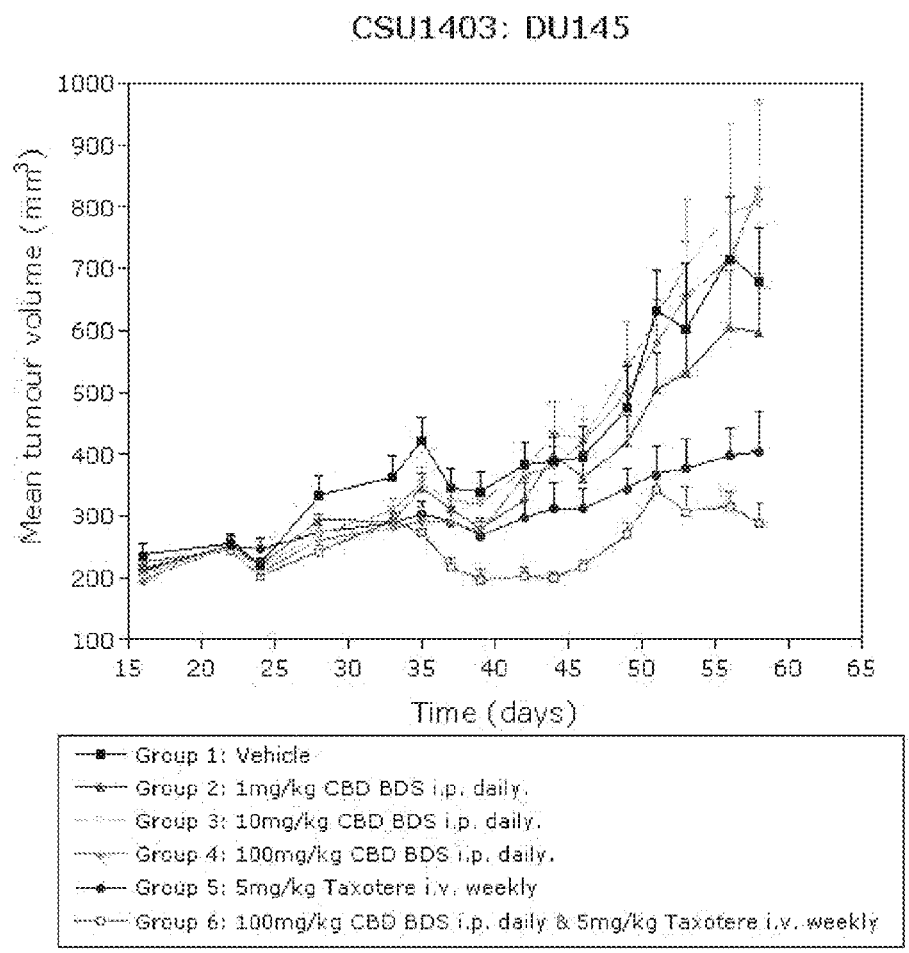

FIGS. 4C and 4D infer that there is little inhibition of tumour volume in the hormone-insensitive (DU-145) prostate cancer cells.

These data all show that phytocannabinoid BDS are very potent compounds for use in the treatment of cancer, particularly when these are combined with another compound such as an anti-androgen or a chemotherapeutic agent.

Example 9

Effect of Phytocannabinoids on Cell Vitality in Breast Cancer Cells (Alamar Blue Assay)

Cells were seeded in presence of FBS in 6 wells multiwell and treated with increased concentrations of compounds for 72 hours. Cell viability was assessed by Alamar blue staining.

Isolated phytocannabinoids were tested on the MDA-MB-231 breast cancer cell line in order to determine whether phytocannabinoids were effective in other types of cancer other than prostate cancer. The different isolated phytocannabinoids chosen for this experiment were: CBGA, CBDA, CBDV, CBD, THCV and THC.

Table 9.1 below details the effectiveness of the cannabinoids at killing the breast cancer cells.

TABLE 9.1

Effect of phytocannabinoids on cell viability of breast cancer cells.

| Compound | IC50 (µM) |
|---|---|
| CBGA | 2.2 |
| CBDA | 3.9 |
| CBDV | 5.0 |
| CBD | 5.0 |
| THCV | 6.5 |
| THC | >10.0 |

The phytocannabinoid acids CBGA and CBDA both appear to be the most efficacious in killing the breast cancer cells and as such make good targets for the use of these compounds in the treatment of cancer. These data show that surprisingly the phytocannabinoid acids are more than 50% better than the free phytocannabinoids.

Example 10

Effect of Phytocannabinoids on Colon Carcinogenesis in the Mouse

The phytocannabinoids isolated CBD, CBG and CBDV and BDS's corresponding to CBD, CBG and CBDV were evaluated in their effect to prevent and treat colon cancer in the mouse. Aberrant crypt focus (ACF), polyps and tumours were induced in the mouse by the carcinogenic substance azoxymethane. The phytocannabinoids were given (i.p.) to the mice three times per week for a period of three months. The COX-2 inhibitor celecoxib was used as a positive control.

Figure 5A:
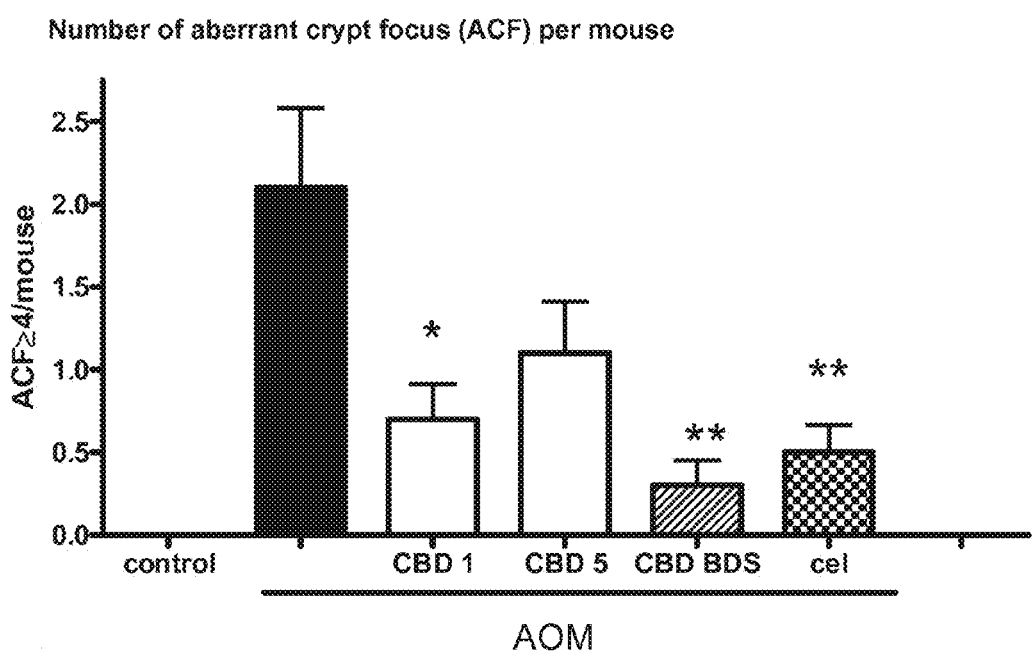
FIGS. 5A-5C show the effect of the cannabinoids isolated CBD and CBD BDS on colon carcinogenesis in the mouse.
Figure 5B:
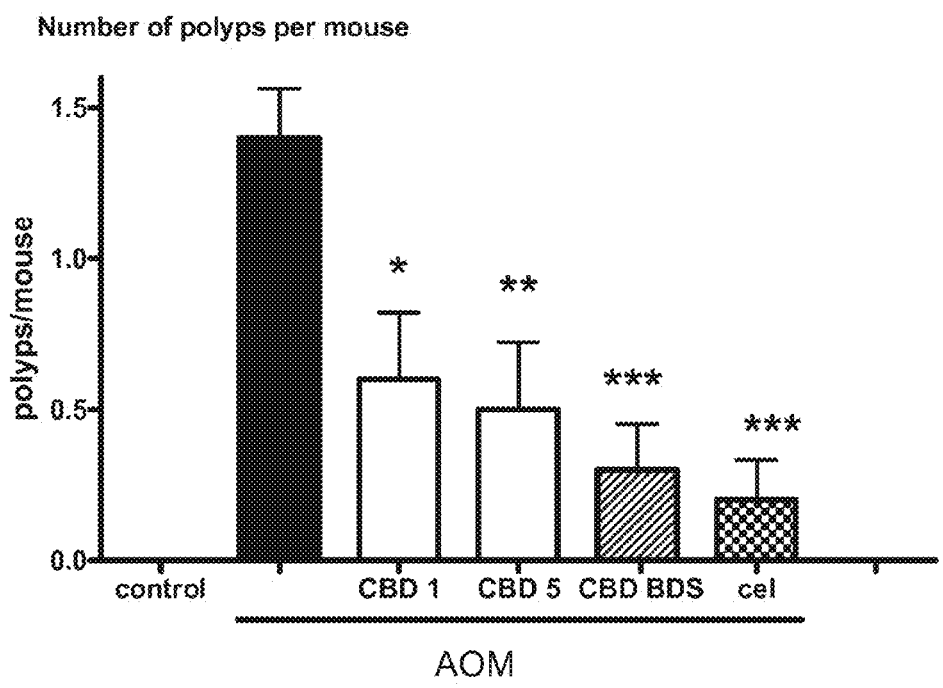
Figure 5C:
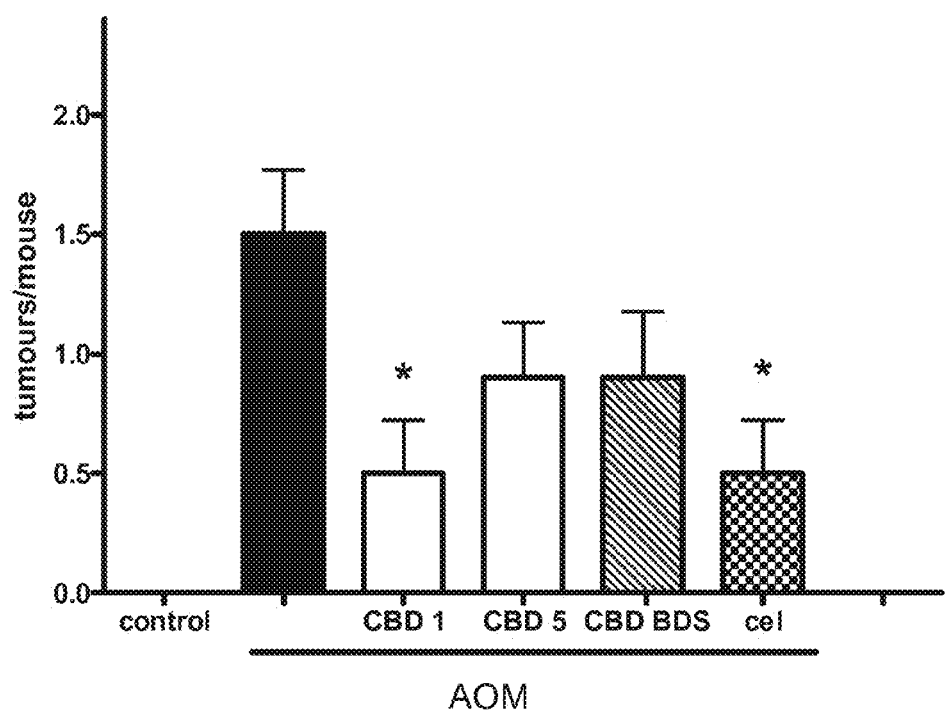

FIGS. 5A-5C detail the results obtained from the experiments with isolated CBD and CBD BDS. In FIG. 5A it can be seen that the CBD BDS is able to statistically significantly reduce the numbers of ACF per mouse in comparison to the control.

FIG. 5B shows that the CBD BDS is more effective at reducing the number of polyps per mouse at a statistically significant level in comparison to the control animals.

FIG. 5C shows that the CBD purified compound significantly reduced the numbers of tumours per animal.

Figure 6A:
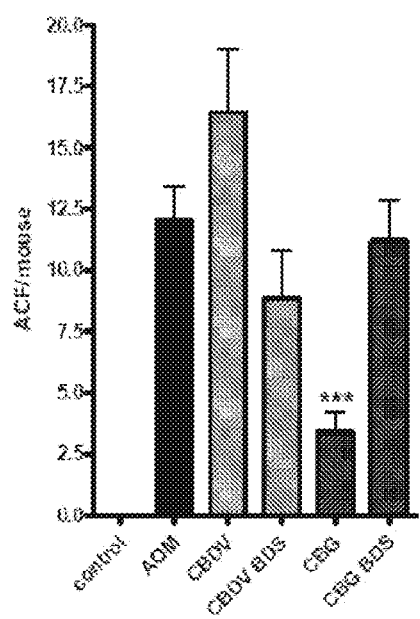
FIGS. 6A-6C show the effect of the cannabinoids isolated CBG, isolated CBDV, CBG BDS and CBDV BDS on colon carcinogenesis in the mouse.
Figure 6B:
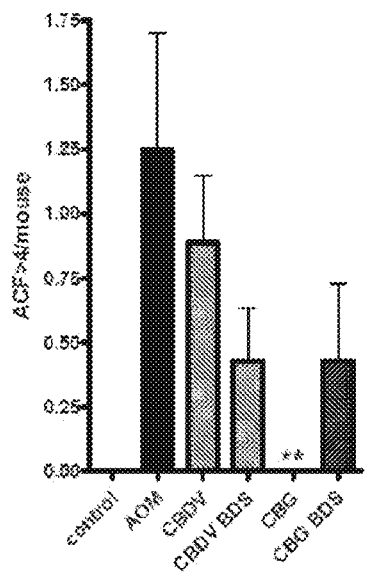
Figure 6C:
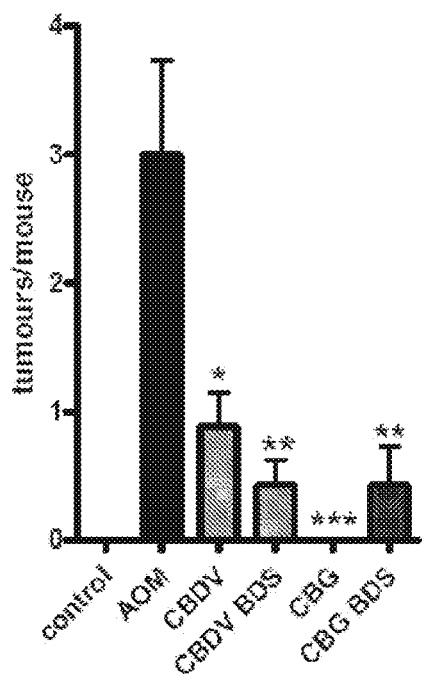

FIGS. 6A-6C demonstrate the data obtained for isolated CBG and CBDV in addition to that obtained for CBG BDS and CBDV BDS.

All of the phyto cannabinoids exerted a protective effect against the experimentally induced colon carcinogenesis as is shown in FIG. 6A with isolated CBG giving the most statistically significant results.

FIG. 6B demonstrates that the protective effect was even more pronounced on the formation of ACF with 4 or more crypts. These type of crypts are predictive of the final incidence of colon cancer and on the formation of tumours. As is shown isolated CBG gave the most statistically significant data demonstrating such a protective effect that there were no ACF with greater than 4 crypts produced in the animals given isolated CBG.

FIG. 6C details the number of tumours that occurred in each animal. Again the data produced in the mice given isolated CBG was such that no tumours were produced in these animals.

In summary these data demonstrate the protective effects of phytocannabinoids in the prevention of colon cancer. Of significance is the phytocannabinoid CBG which exerts a strong protective effect against colon cancer particularly when it is in an isolated form.

Example 11

Effect of Phytocannabinoids in Human Glioma Cells on Cell Vitality (MTT Assay)

Cells were seeded in presence of FBS in 6 wells multiwell with a density of $8 \times 10^4$ cells/well. Glioma cells were treated with increased concentrations of compounds and cell viability was assessed by MTT staining.

CBD BDS and isolated CBD, CBG and CBDV were tested.

Table 11.1 details the data observed. As can be seen the CBD BDS gave the best result with the lowest concentration being a little more effective than its respective isolated phytocannabinoid.

TABLE 11.1

Effect of phytocannabinoids on cell vitality (MTT Assay)

| Sample | $IC_{50}$ on glioma cell vitality |
|---|---|
| CBD | 8.92 µM |
| CBD BDS | 8.83 µM |
| CBG | 12.40 µM |
| CBDV | 12.40 µM |

As can be observed these data indicate that both CBD BDS and isolated CBD might be useful treatments in brain tumours including glioma.

Example 12

Effect of the Cannabinoids THC and CBD Alone and in Combination with Each Other and/or the Chemotherapeutic Agent Temazolamide on the Viability of Human Glioma Cell Lines (MTT Assay)

The synergistic action of the combined administration of the phytocannabinoids THC and CBD in equal amounts was tested in human glioma cell lines. The combined administration of the two phytocannabinoids led to a synergic reduction in the viability of human glioma cells during an MTT assay.

Table 12.1 below shows that the sub-effective dose levels of THC and CBD (0.7 μM) leads to a statistically significant reduction in cell viability when the two cannabinoids are combined. The cell viability is dramatically reduced when the dose level of the THC and CBD are increased.

TABLE 12.1

Cell viability of U87 glioma cells treated with THC, CBD and THC:CBD (1:1)

| Compound | Dose level (μM) | Cell Viability (%) |
|---|---|---|
| Control | — | 100 |
| THC | 0.7 | 100 |
| CBD | 0.7 | 115 |
| THC:CBD (1:1) | 0.7 (each) | 90 |
| THC | 0.9 | 92 |
| CBD | 0.9 | 95 |
| THC:CBD (1:1) | 0.9 (each) | 70 |
| THC | 1.2 | 80 |
| CBD | 1.2 | 70 |
| THC:CBD (1:1) | 1.2 (each) | 35 |

Further experiments were undertaken using the chemotherapeutic agent temazolamide (TMZ) these data are shown in Table 12.2 below.

TABLE 12.2

Cell viability of U87 glioma cells treated with THC, CBD, THC:CBD (1:1) and TMZ

| Compound | Cell Viability (%) |
|---|---|
| Control | 100 |
| THC (1 μM) | 115 |
| CBD (1 μM) | 98 |
| TMZ (100 μM) | 82 |
| THC:CBD (1 μM each) | 55 |
| THC (1 μM) + TMZ (100 μM) | 70 |
| CBD (1 μM) + TMZ (100 μM) | 65 |
| THC:CBD (1 μM each) + TMZ (100 μM) | 38 |

The combined administration of sub-maximal doses of THC, CBD and TMZ led to a synergic reduction of the viability of the U87 glioma cells.

Example 13

Effect of the Cannabinoids THC and CBD Alone and in Combination with Each Other and/or the Chemotherapeutic Agent Temazolamide on the Viability of Human Glioma Xenografts

TABLE 13.1

Tumour volume after treatment with THC, CBD and THC:CBD (1:1)

| Compound | Dose level (mg/kg) | Tumour volume (increase from day 1) |
|---|---|---|
| Control | — | 10.3 |
| THC | 3.7 | 8.7 |
| CBD | 3.7 | 9.1 |
| THC:CBD (1:1) | 3.7 (each) | 8.9 |
| THC | 7.5 | 8.5 |
| CBD | 7.5 | 8.9 |
| THC:CBD (1:1) | 7.5 (each) | 5.7 |
| THC | 15.0 | 5.8 |
| CBD | 15.0 | 7.6 |

The phytocannabinoids were also tested with the TMZ as is detailed in Table 13.2 below.

TABLE 13.2

Tumour volume after treatment with THC, CBD, THC:CBD (1:1) and TMZ

| Compound | Tumour volume (increase from day 1) |
|---|---|
| Control | 10.3 |
| THC:CBD (3.7 mg/kg each) | 8.9 |
| TMZ (100 μM) | 4.1 |
| THC:CBD (3.7 mg/kg each) + TMZ (100 μM) | 2.6 |

The following paragraphs are not claims, but represent preferred aspects and embodiments of the invention.

1. A *cannabis* plant extract comprising a phytocannabinoid containing component and a non-phytocannabinoid containing component, for use in medicine, wherein the phytocannabinoid containing component comprises at least 50% (w/w) of the *cannabis* plant extract and the non-phytocannabinoid containing component comprises a monoterpene fraction and a sesquiterpene fraction, in which a principle monoterpene sub-fraction is selected from myrcenes or pinenes and a principle sesquiterpene sub-fraction is selected from caryophyllenes or humulenes.

2. The use of a *cannabis* plant extract comprising a phytocannabinoid containing component and a non-phytocannabinoid containing component, for use in the manufacture of a medicament for use in medicine, wherein the phytocannabinoid containing component comprises at least 50% (w/w) of the *cannabis* plant extract and the non-phytocannabinoid containing component comprises a monoterpene fraction and a sesquiterpene fraction and wherein a principle monoterpene sub-fraction is selected from myrcenes or pinenes and a principle sesquiterpene sub-fraction is selected from caryophyllenes or humulenes.

3. A *cannabis* plant extract or the use of a *cannabis* plant extract as claimed in paragraphs 1 and 2, for use in the treatment of cancer.

4. A *cannabis* plant extract or the use of a *cannabis* plant extract as claimed in paragraphs 1-3, wherein the principle monoterpene sub-fraction comprises myrcenes and the secondary monoterpene sub-fraction comprises pinenes.

5. A *cannabis* plant extract or the use of a *cannabis* plant extract as claimed in paragraphs 1-4, wherein the principle monoterpenes sub-fraction comprises both myrcenes and pinenes.

6. A *cannabis* plant extract or the use of a *cannabis* plant extract as claimed in any of the preceding paragraphs, wherein the principle sesquiterpene sub-fraction comprises caryophyllenes and secondary sesquiterpene sub-fraction comprises humulenes.

7. A *cannabis* plant extract or the use of a *cannabis* plant extract as claimed in any of the preceding paragraphs, wherein the principle phytocannabinoid is selected from the group consisting of: THCV, CBDV, CBGV, THCVA, THCA, CBDA, CBG, THC, CBD and CBC.

8. A *cannabis* plant extract or the use of a *cannabis* plant extract as claimed in any of the preceding paragraphs, wherein the non-phytocannabinoid containing component further comprises one or more compounds from the group consisting of: diterpenes; triterpenes; sterols; triglycerides; alkanes; squalenes; tocopherols; and carotenoids.

9. A *cannabis* plant extract or the use of a *cannabis* plant extract as claimed in any of the preceding paragraphs, wherein the principle phytocannabinoid is CBG and the phytocannabinoid containing component comprises 61-75% (w/w) of the *cannabis* plant extract.

10. A *cannabis* plant extract or the use of a *cannabis* plant extract as claimed in paragraph 9, comprising greater than 88% (w/w) CBG of the total phytocannabinoid fraction.

11. A *cannabis* plant extract or the use of a *cannabis* plant extract as claimed in any of paragraphs 1-8, wherein the principle phytocannabinoid is THC and the phytocannabinoid containing component comprises 77-94% (w/w) of the *cannabis* plant extract.

12. A *cannabis* plant extract or the use of a *cannabis* plant extract as claimed in paragraph 11, comprising 78-95% (w/w) THC of the total phytocannabinoid fraction.

13. A *cannabis* plant extract or the use of a *cannabis* plant extract as claimed in any of paragraphs 1-8, wherein the principle phytocannabinoid is CBD and the phytocannabinoid containing component comprises 76-96% (w/w) of the *cannabis* plant extract.

14. A *cannabis* plant extract or the use of a *cannabis* plant extract as claimed in paragraph 13, comprising 72-88% (w/w) CBD of the total phytocannabinoid fraction.

15. A *cannabis* plant extract or the use of a *cannabis* plant extract as claimed in any of paragraphs 1-8, wherein the principle phytocannabinoid is CBC and the phytocannabinoid containing component comprises 49-60% (w/w) of the *cannabis* plant extract.

16. A *cannabis* plant extract or the use of a *cannabis* plant extract as claimed in paragraph 15, comprising 71-87% (w/w) CBC of the total phytocannabinoid fraction.

17. A *cannabis* plant extract or the use of a *cannabis* plant extract as claimed in paragraph 16, which further comprises the secondary phytocannabinoids CBD and CBL.

18. A *cannabis* plant extract or the use of a *cannabis* plant extract as claimed in paragraph 17, wherein the CBD comprises 6.5-8% (w/w) of the total phytocannabinoid fraction and the CBL comprises 5.8-7.1 (w/w) of the total phytocannabinoid fraction.

19. A *cannabis* plant extract or the use of a *cannabis* plant extract as claimed in any of paragraphs 1-8, wherein the principle phytocannabinoid is THCV and the phytocannabinoid containing component comprises 74-90% (w/w) of the *cannabis* plant extract.

20. A *cannabis* plant extract or the use of a *cannabis* plant extract as claimed in paragraph 19, comprising 71-87% (w/w) THCV of the total phytocannabinoid fraction.

21. A *cannabis* plant extract or the use of a *cannabis* plant extract as claimed in paragraph 20, which further comprises the secondary phytocannabinoid THC.

22. A *cannabis* plant extract or the use of a *cannabis* plant extract as claimed in paragraph 21, wherein the THC comprises 14.8-18% (w/w) of the total phytocannabinoid fraction.

23. A *cannabis* plant extract or the use of a *cannabis* plant extract as claimed in any of paragraphs 1-8, wherein the principle phytocannabinoid is CBDV and the phytocannabinoid containing component comprises 64-78% (w/w) of the *cannabis* plant extract.

24. A *cannabis* plant extract or the use of a *cannabis* plant extract as claimed in paragraph 23, comprising 52-64% (w/w) CBDV of the total phytocannabinoid fraction.

25. A *cannabis* plant extract or the use of a *cannabis* plant extract as claimed in paragraph 24, which further comprises the secondary phytocannabinoids CBD and CBCV.

26. A *cannabis* plant extract or the use of a *cannabis* plant extract as claimed in paragraph 25, wherein the CBD comprises 22.4-27.4% (w/w) of the total phytocannabinoid fraction and the CBCV comprises 5.5-6.7 (w/w) of the total phytocannabinoid fraction.

27. A *cannabis* plant extract or the use of a *cannabis* plant extract as claimed in any of paragraphs 1-8, wherein the principle phytocannabinoid is CBGV and the phytocannabinoid containing component comprises 54-66% (w/w) of the *cannabis* plant extract.

28. A *cannabis* plant extract or the use of a *cannabis* plant extract as claimed in paragraph 27, comprising 68-84% (w/w) CBGV of the total phytocannabinoid fraction.

29. A *cannabis* plant extract or the use of a *cannabis* plant extract as claimed in paragraph 28, which further comprises the secondary phytocannabinoid CBG.

30. A *cannabis* plant extract or the use of a *cannabis* plant extract as claimed in paragraph 29, wherein the CBG comprises 19-23% (w/w) of the total phytocannabinoid fraction.

31. A *cannabis* plant extract or the use of a *cannabis* plant extract as claimed in any of paragraphs 1-8, wherein the principle phytocannabinoid is THCA and the phytocannabinoid containing component comprises 54-66% (w/w) of the *cannabis* plant extract.

32. A *cannabis* plant extract or the use of a *cannabis* plant extract as claimed in paragraph 31, comprising 71-86% (w/w) THCA of the total phytocannabinoid fraction.

33. A *cannabis* plant extract or the use of a *cannabis* plant extract as claimed in paragraph 32, which further comprises the secondary phytocannabinoid THC.

34. A *cannabis* plant extract or the use of a *cannabis* plant extract as claimed in paragraph 33, wherein the THC comprises 13.4-16.4% (w/w) of the total phytocannabinoid fraction.

35. A *cannabis* plant extract or the use of a *cannabis* plant extract as claimed in any of paragraphs 1-8, wherein the principle phytocannabinoid is CBDA and the phytocannabinoid containing component comprises 71-86% (w/w) of the *cannabis* plant extract.

36. A *cannabis* plant extract or the use of a *cannabis* plant extract as claimed in paragraph 35, comprising 78-86% (w/w) CBDA of the total phytocannabinoid fraction.

37. A *cannabis* plant extract or the use of a *cannabis* plant extract as claimed in paragraph 36, which further comprises the secondary phytocannabinoid CBD.

38. A *cannabis* plant extract or the use of a *cannabis* plant extract as claimed in paragraph 37, wherein the CBD comprises 6.1-7.5% (w/w) of the total phytocannabinoid fraction.

39. A *cannabis* plant extract or the use of a *cannabis* plant extract as claimed in any of paragraphs 1-8, wherein the principle phytocannabinoid is THCVA and the phytocannabinoid containing component comprises 62-75% (w/w) of the *cannabis* plant extract.

40. A *cannabis* plant extract or the use of a *cannabis* plant extract as claimed in paragraph 39, comprising 53-65% (w/w) THCVA of the total phytocannabinoid fraction.

41. A *cannabis* plant extract or the use of a *cannabis* plant extract as claimed in paragraph 40, which further comprises the secondary phytocannabinoid THCV.

42. A *cannabis* plant extract or the use of a *cannabis* plant extract as claimed in paragraph 41, wherein the THCV comprises 17.3-21.2% (w/w) of the total phytocannabinoid fraction.

43. A method of treating a patient comprising administering a therapeutically effective amount of a *cannabis* plant extract comprising a phytocannabinoid containing component and a non-phytocannabinoid containing component, wherein the phytocannabinoid containing component comprises at least 50% (w/w) of the *cannabis* plant extract and the non-phytocannabinoid containing component comprises a monoterpene fraction and a sesquiterpene fraction, in which a principle monoterpene sub-fraction is selected from myrcenes or pinenes and a principle sesquiterpene sub-fraction is selected from caryophyllenes or humulenes to the patient.

44. The use of one or more phytocannabinoids, either in an isolated form or in the form of a botanical drug substance (BDS), as a prophylactic or in the treatment of cancer 45. One or more phytocannabinoids, selected from the group consisting of: THCV, CBDV, THCVA, THCA, CBDA, CBD, CBG, and CBC, for use in the treatment of prostate cancer, wherein, where present, the THCVA is present as an isolated phytocannabinoid, the THCA, CBDA, CBD, CBG or CBC are present in the form of a BDS, and the THCV or CBDV are present in either an isolated form or in the form of a BDS.

46. The use of one or more phytocannabinoids, selected from the group consisting of: THCV, CBDV, THCVA, THCA, CBDA, CBD, CBG, and CBC, for use in the manufacture of a medicament to treat of prostate cancer, wherein, where present, the THCVA is present as an isolated phytocannabinoid, the THCA, CBDA, CBD, CBG or CBC are present in the form of a BDS, and the THCV or CBDV are present in either an isolated form or in the form of a BDS.

47. The one or more phytocannabinoids or the use of one or more phytocannabinoids as claimed in paragraph 45 or 46, wherein the one or more phytocannabinoids are propyl variant phytocannabinoids.

48. The one or more phytocannabinoids or the use of one or more phytocannabinoids as claimed in paragraph 45 or 46, wherein the one or more phytocannabinoids are in an acid form.

49. The one or more phytocannabinoids or the use of one or more phytocannabinoids as claimed in paragraph 45 or 46, wherein the one or more phytocannabinoids are in a neutral or decarboxylated form.

50. The one or more phytocannabinoids or the use of one or more phytocannabinoids as claimed in paragraph 45 or 46, wherein the phytocannabinoid is CBG and is in the form of a BDS.

51. The one or more phytocannabinoids or the use of one or more phytocannabinoids as claimed in any of the paragraphs 45 to 50, wherein the prostate cancer is hormone-sensitive prostate cancer.

52. The one or more phytocannabinoids or the use of one or more phytocannabinoids as claimed in paragraph 51, wherein the phytocannabinoid is THCVA in an isolated form.

53. The one or more phytocannabinoids or the use of one or more phytocannabinoids as claimed in any of the paragraphs 45 to 50, wherein the prostate cancer is hormone-insensitive prostate cancer.

54. The one or more phytocannabinoids or the use of one or more phytocannabinoids as claimed in paragraph 53, wherein the phytocannabinoid is CBD and is in the form of a BDS.

55. The one or more phytocannabinoids or the use of one or more phytocannabinoids as claimed in paragraph 53, wherein the phytocannabinoid is CBDV and is in the form of a BDS.

56. The one or more phytocannabinoids or the use of one or more phytocannabinoids as claimed in paragraph 45 or 46, wherein the one or more phytocannabinoids are used in combination or as an adjunct therapy with a chemotherapeutic agent and/or an anti-androgen.

57. The use as claimed in paragraph 56, wherein the chemotherapeutic agent is a mitotic inhibitor.

58. The use as claimed in paragraph 57, wherein the mitotic inhibitor is from the taxane drug class.

59. The use as claimed in paragraph 58, wherein the mitotic inhibitor from the taxane drug class is taken from the group: docetaxel; larotaxel; ortataxel; paclitaxel; and tesetaxel.

60. The one or more phytocannabinoids or the use of one or more phytocannabinoids as claimed in paragraph 56, wherein the phytocannabinoid is CBG.

61. The one or more phytocannabinoids or the use of one or more phytocannabinoids as claimed in paragraph 56, wherein the phytocannabinoid is CBD.

62. The one or more phytocannabinoids or the use of one or more phytocannabinoids as claimed in paragraph 60 or 61, wherein the phytocannabinoid is in the form of a BDS.

63. The one or more phytocannabinoids or the use of one or more phytocannabinoids as claimed in paragraph 62, for the purpose of slowing down the growth or reducing the volume of a prostate cancer tumour.

64. A method of treating a patient with prostate cancer comprising administering an effective amount of one or more phytocannabinoids, selected from the group consisting of: THCV, CBDV, THCVA, THCA, CBDA, CBD, CBG, and CBC, wherein, where present, the THCVA is present as an isolated phytocannabinoid, the THCA, CBDA, CBD, CBG or CBC are present in the form of a BDS, and the THCV or CBDV are present in either an isolated form or in the form of a BDS to the patient.

65. One or more propyl phytocannabinoids or acid phytocannabinoids for use in the down regulation of ERK signalling and effect one or more of: anti-proliferation, anti-metastasis or anti-angiogenesis in a human patient.

66. The use of one or more propyl phytocannabinoids or acid phytocannabinoids in the manufacture of a medicament to down regulate ERK signalling and effect one or more of: anti-proliferation, anti-metastasis or anti-angiogenesis in a human patient.

67. The one or more propyl or acid phytocannabinoids or the use of one or more propyl or acid phytocannabinoids as claimed in paragraph 65 or 66, wherein the phytocannabinoids is selected from the group consisting of: THCV, CBGV, CBDV, CBGA and CBDA.

68. The one or more propyl or acid phytocannabinoids or the use of one or more propyl or acid phytocannabinoids as claimed in any of paragraphs 65-67, wherein the phytocannabinoid is in an isolated form.

69. The one or more propyl or acid phytocannabinoids or the use of one or more propyl or acid phytocannabinoids as claimed in any of paragraphs 65-68, for use in the treatment of lung cancer, prostate cancer, or breast cancer.

70. The one or more propyl or acid phytocannabinoids or the use of one or more propyl or acid phytocannabinoids as claimed in paragraph 69, for use in the treatment of bone or lymph metastasis.

71. A method of treating a patient with cancer comprising administering one or more propyl phytocannabinoids or acid phytocannabinoids to down regulate ERK signalling and effect one or more of: anti-proliferation, anti-metastasis or anti-angiogenesis to the patient.

72. One or more phytocannabinoid acids, excluding CBDA or CBDVA, for use in medicine.

73. One or more phytocannabinoid acids for use in the treatment of cancer.

74. The use of one or more phytocannabinoid acids in the manufacture of a medicament for use in the treatment of cancer.

75. One or more phytocannabinoid acids or the use of one or more phytocannabinoid acids as claimed in any of paragraphs 72 to 74, wherein the one or more phytocannabinoid acid are in the form of a BDS.

76. One or more phytocannabinoid acids or the use of one or more phytocannabinoid acids as claimed in paragraphs 72-75, wherein the cancer to be treated is a cancer of the prostate, breast, colon, lung, glioma or skin.

77. One or more phytocannabinoid acids or the use of one or more phytocannabinoid acids as claimed in paragraphs 72-76, wherein the phytocannabinoid acid is taken from the group consisting of: THCA, CBGA and CBDA.

78. One or more phytocannabinoid acids or the use of one or more phytocannabinoid acids as claimed in paragraphs 72-77, comprising in combination the phytocannabinoid THCA with CBDA and/or CBGA.

79. A method of treating cancer comprising administering a therapeutic amount of one or more phytocannabinoid acids to a patient.

80. An isolated CBD, CBG, CBDV, CBD BDS, CBG BDS and/or CBDV BDS for use in the treatment of a pre-cancerous symptom of colon cancer.

81. The use of isolated CBD CBG, CBDV, CBD BDS, CBG BDS and/or CBDV BDS in the manufacture of a medicament for use to treat a pre-cancerous symptom of colon cancer.

82. Isolated CBD CBG, CBDV, CBD BDS, CBG BDS and/or CBDV BDS or use of isolated CBD CBG, CBDV, CBD BDS, CBG BDS and/or CBDV BDS as claimed in paragraph 80 or 81, wherein the isolated CBD CBG, CBDV, CBD BDS, CBG BDS and/or CBDV BDS are used in the treatment of aberrant crypts in the colon.

83. Isolated CBD CBG, CBDV, CBD BDS, CBG BDS and/or CBDV BDS or use of isolated CBD CBG, CBDV, CBD BDS, CBG BDS and/or CBDV BDS as claimed in paragraph 80 or 81, wherein the isolated CBD CBG, CBDV, CBD BDS, CBG BDS and/or CBDV BDS are used in the treatment of colon polyps.

84. A method of treating a patient with a pre-cancerous symptom of colon cancer, comprising administering a therapeutically effective amount of an isolated CBD CBG, CBDV, CBD BDS, CBG BDS and/or CBDV BDS to the patient.

85. A combination of phytocannabinoids together with a chemotherapeutic agent which is not a cannabinoid, for use in the treatment of a glioma.

86. The use of a combination of phytocannabinoids together with a chemotherapeutic agent which is not a cannabinoid, in the manufacture of a medicament to treat a glioma.

87. The combination of phytocannabinoids or the use of the combination of phytocannabinoids as claimed in paragraph 85 or paragraph 86, wherein the combination of phytocannabinoids and the chemotherapeutic agent which is not a cannabinoid are packaged for administration separately, simultaneously or sequentially.

88. The combination of phytocannabinoids or the use of the combination of phytocannabinoids as paragraphed in paragraphs 85-87, wherein the phytocannabinoids are THC and CBD.

89. The combination of phytocannabinoids or the use of the combination of phytocannabinoids as claimed in paragraphs 85-88, wherein the dose level of the phytocannabinoids is sub-effective for the treatment of the glioma if used alone.

90. The combination of phytocannabinoids or the use of the combination of phytocannabinoids as claimed in paragraphs 85-89, wherein the chemotherapeutic agent is temazolamide.

91. The combination of phytocannabinoids or the use of the combination of phytocannabinoids as claimed in paragraphs 85-90, wherein the dose level of the temazolamide is sub-effective for the treatment of the glioma if used alone.

92. A method of treating a patient with a glioma, comprising administering a therapeutically effective amount of a combination of phytocannabinoids together with a chemotherapeutic agent which is not a cannabinoid, to the patient.

The invention claimed is:

1. A pharmaceutical product consisting essentially of (1) isolated CBD and temazolamide, (2) isolated THC and temazolamide, or (3) a combination of isolated CBD, isolated THC and temazolamide, wherein the pharmaceutical product is packaged for administration separately, simultaneously or sequentially.

* * * * *